(12) United States Patent
Culhane et al.

(10) Patent No.: US 11,678,894 B2
(45) Date of Patent: Jun. 20, 2023

(54) KNEE BALANCING INSTRUMENT

(71) Applicant: DEPUY IRELAND UNLIMITED COMPANY, Ringaskiddy (IE)

(72) Inventors: Chris Culhane, Melbourne (AU); Peter J McMahon, Melbourne (AU); Grant Mellor, Eltham (AU)

(73) Assignee: Jonathan P. Cabot, North Adelaide (AU)

( * ) Notice: Subject to any disclaimer, the term of this patent is extended or adjusted under 35 U.S.C. 154(b) by 0 days.

(21) Appl. No.: 16/769,367

(22) PCT Filed: Dec. 14, 2018

(86) PCT No.: PCT/EP2018/084887
§ 371 (c)(1),
(2) Date: Jun. 3, 2020

(87) PCT Pub. No.: WO2019/115744
PCT Pub. Date: Jun. 20, 2019

(65) Prior Publication Data
US 2021/0177439 A1    Jun. 17, 2021

Related U.S. Application Data

(60) Provisional application No. 62/599,070, filed on Dec. 15, 2017.

(51) Int. Cl.
*A61B 17/02* (2006.01)
*A61B 17/17* (2006.01)
(Continued)

(52) U.S. Cl.
CPC ........ *A61B 17/1764* (2013.01); *A61B 17/025* (2013.01); *A61F 2/389* (2013.01);
(Continued)

(58) Field of Classification Search
CPC ........... A61B 17/025; A61B 2017/0268; A61F 2/4455; A61F 2002/30413; A61F 2/461
See application file for complete search history.

(56) References Cited

U.S. PATENT DOCUMENTS 3,750,652 A    8/1973   Sherwin
4,501,266 A    2/1985   McDaniel
(Continued)

FOREIGN PATENT DOCUMENTS

EP    1348382 A2    10/2003
EP    1915951 A2    4/2008
(Continued)

OTHER PUBLICATIONS

LCS Complete Mobile-Bearing Knee System, Surgical Technique, 3M1001, 0611-63-050 (Rev. 2), 2001 (44 Pages).
(Continued)

*Primary Examiner* — Samuel S Hanna
(74) *Attorney, Agent, or Firm* — Renner, Kenner, Greive, Bobak, Taylor & Weber

(57) ABSTRACT

Disclosed is an instrument for balancing a knee. The instrument has a first plate (10) coupled to a second plate (50) by a plurality of adjusters (152A, 152B, 152C). The adjusters are actuatable to vary the gap between the first and second plates. Each adjuster is coupled to the second plate by a joint having at least two degrees of freedom. Also disclosed is an outrigger (300). The outrigger includes a body featuring a connection component configured to be received and held by a slot (34) of the instrument. The slot is arranged to align a blade of a surgical saw with a portion of a knee to be cut. Also disclosed is a method of balancing a knee using the instrument and a method of fabricating the instrument.

16 Claims, 19 Drawing Sheets

(51) Int. Cl.
*A61F 2/38* (2006.01)
*A61F 2/30* (2006.01)

(52) U.S. Cl.
CPC .... *A61F 2/3859* (2013.01); *A61B 2017/0268* (2013.01); *A61F 2002/30537* (2013.01)

(56) References Cited

U.S. PATENT DOCUMENTS

| | | | |
|---|---|---|---|
| 4,566,448 | A | 1/1986 | Rohr, Jr. |
| 4,898,161 | A | 2/1990 | Grundei |
| 4,938,762 | A | 7/1990 | Wehrli |
| 5,431,653 | A | 7/1995 | Callaway |
| 5,540,696 | A | 7/1996 | Booth, Jr. |
| 5,597,379 | A | 1/1997 | Haines |
| 5,649,929 | A | 7/1997 | Callaway |
| 5,733,292 | A | 3/1998 | Gustilo |
| 5,800,438 | A | 9/1998 | Tuke |
| 5,871,542 | A | 2/1999 | Goodfellow et al. |
| 5,911,723 | A | 6/1999 | Ashby |
| 5,931,777 | A | 8/1999 | Sava |
| 5,989,290 | A | 11/1999 | Biedermann |
| 6,022,377 | A | 2/2000 | Nuelle |
| 6,159,217 | A | 12/2000 | Robie |
| 6,261,296 | B1 | 7/2001 | Aebi |
| 6,648,896 | B2 | 11/2003 | Overes |
| 6,719,796 | B2 | 4/2004 | Cohen |
| 7,156,853 | B2 | 1/2007 | Muratsu |
| 7,309,363 | B2 | 12/2007 | Dietz |
| 7,635,369 | B2 | 12/2009 | Cinquin |
| 7,976,550 | B2 | 7/2011 | Trudeau |
| 8,137,361 | B2 | 3/2012 | Duggineni |
| 8,197,489 | B2 | 6/2012 | Chesser et al. |
| 8,303,663 | B2 | 11/2012 | Jimenez et al. |
| 8,337,508 | B2 | 12/2012 | Lavalle |
| 9,078,669 | B2 | 7/2015 | Dower |
| 9,386,975 | B2 | 7/2016 | Markworth et al. |
| 9,592,133 | B2 | 3/2017 | Toler |
| 9,782,249 | B2 | 10/2017 | Hauri |
| 2002/0123754 | A1 | 9/2002 | Holmes |
| 2002/0156480 | A1 | 10/2002 | Overes |
| 2002/0165550 | A1 | 11/2002 | Frey |
| 2003/0225416 | A1 | 12/2003 | Bonvallet |
| 2004/0097951 | A1 | 5/2004 | Steffensmeier |
| 2004/0106927 | A1 | 6/2004 | Ruffner |
| 2004/0122441 | A1 | 6/2004 | Muratsu |
| 2004/0172129 | A1 | 9/2004 | Schafer |
| 2004/0249387 | A1 | 12/2004 | Faoro |
| 2005/0020941 | A1 | 1/2005 | Tarabichi |
| 2005/0059980 | A1 | 3/2005 | Overes |
| 2005/0085920 | A1 | 4/2005 | Williamson |
| 2005/0177173 | A1 | 8/2005 | Aebi |
| 2006/0074432 | A1 | 4/2006 | Stad |
| 2007/0233144 | A1 | 10/2007 | Lavallee |
| 2007/0239157 | A1 | 10/2007 | Guillaume |
| 2008/0051798 | A1 | 2/2008 | Colquhoun |
| 2008/0114367 | A1 | 5/2008 | Meyer |
| 2009/0043310 | A1 | 2/2009 | Rasmussen |
| 2009/0222089 | A1 | 9/2009 | Hauri |
| 2010/0249789 | A1 | 9/2010 | Rock |
| 2010/0305575 | A1 | 12/2010 | Wilkinson et al. |
| 2012/0158152 | A1 | 6/2012 | Claypool |
| 2013/0102929 | A1* | 4/2013 | Haight .......... A61F 2/4657 600/587 |
| 2014/0094715 | A1 | 4/2014 | Stein et al. |
| 2015/0230804 | A1 | 8/2015 | Chana |
| 2016/0346098 | A1 | 12/2016 | Uthgenannt |
| 2017/0312099 | A1 | 11/2017 | Paszicsnyek |
| 2019/0110905 | A1 | 4/2019 | Cabot |
| 2020/0155135 | A1 | 5/2020 | Cole |

FOREIGN PATENT DOCUMENTS

| | | | |
|---|---|---|---|
| GB | 2198647 | A | 6/1998 |
| WO | WO1997009939 | A1 | 3/1997 |
| WO | 1999035972 | A1 | 7/1999 |
| WO | 2000019911 | A2 | 4/2000 |
| WO | 2001085038 | A8 | 2/2002 |
| WO | 2002087466 | A3 | 2/2003 |
| WO | 2002071924 | B1 | 3/2003 |
| WO | 2003084412 | A1 | 10/2003 |
| WO | 2006136836 | A2 | 12/2006 |
| WO | 2008021972 | A2 | 2/2008 |
| WO | 2010116394 | A1 | 10/2010 |
| WO | 2011128657 | A1 | 10/2011 |
| WO | 2012020460 | A1 | 2/2012 |
| WO | 2016065396 | A1 | 5/2012 |
| WO | WO2016065396 | A1 | 5/2016 |

OTHER PUBLICATIONS

AMK Congruency Instrument System, Surgical Technique, 2.7M1198, 0612-76-000, 1997 (16 Pages).
Knee Balancer Complementing PFC Sigma and LCS Complete EGF Instrumentation, Reference Guide and Surgical Technique, 4M0703, 0612-21-500, 2003 (15 pages).
NJ LCS® Unicompartmental Knee System with Porocoat®, Surgical Procedure by Frederick F. Buechel, M.D., Biomedical Engineering Trust, South Orange NJ, 1994, (11 Pages).
Rand, James A., M.D., Total Knee Arthroplasty, 1993 by Mayo Foundation, Raven Press, New York, 1993, (8 Pages).
New Jersey LCS® Total Knee System, Surgical Technique, Using Milestone™ Instruments, R. Barry Sorrells, M.D. and Frederick F. Buechel, M.D., DePuy, 20MO104, 0601-87, 1994, (57 Pages).
Attune Knee System, Intuition Instruments—KNEE3 Surgical Technique, Depuy Synthes, DSUS/JRC/0516/1579 (Rev. 1) 03/18; DSEM/JRC/0118/0996 (Rev 1) 03/18, 114 Pages (2018).
Zimmer FuZION Instruments Surgical Technique, 97-5026-046-00 REV. 1, MC126382 Aug. 30, 2016, 2016 Zimmer, Inc., 44 Pages.

* cited by examiner

KNEE BALANCING INSTRUMENT

This application is a National Stage Application filed Under 35 U.S.C. § 371 of International Application No. PCT/EP2018/084887 filed Dec. 14, 2018, which claims priority to U.S. provisional application 62/599,070 filed Dec. 15, 2017, which are both hereby incorporated by reference in their entireties.

FIELD OF THE INVENTION

The present disclosure relates to surgical instruments, kits and methods for balancing a knee during a surgical knee replacement procedure.

DESCRIPTION OF THE RELATED ART

A knee is a joint located between a femur and a tibia of a person or animal. The knee includes various bone structure and soft tissue including cartilage, muscles, tendons and ligaments. The knee may be damaged in a variety of ways including rheumatoid arthritis, osteoarthritis and traumatic injury. A knee so damaged may need replacing totally or partially by a knee replacement implant.

A physician will typically operate on the knee to remove portions of the knee and replace them with a total or partial knee replacement implant. Typically, the physician will seek to restore the knee to a healthy condition in which it will be as close as possible to condition of the knee before the damage occurred. In order to achieve such a restoration, a physician may select knee replacement implants of an appropriate size out of a range of sizes.

During a surgical procedure, a physician seeks to replace a patient's knee joint with an implant offering an optimal soft tissue balance. The correct balance is sought to keep the joint aligned in flexion and extension as a patient goes about daily activities such as, for example, walking, bending, and sitting. Optimal balancing can also improve the durability and longevity of the implants.

To check the soft tissue, balance a physician may perform a series of checks and take a series of measurements. These checks and measurement may involve using a variety of instruments to identify whether a knee would be optimally balanced if a particular size of implant was used to replace a patient's knee joint.

A known instrument for such a procedure is disclosed in a patent cooperation treaty patent application having the publication number WO2016065396. In WO2016065396, an arrangement for the preparation of the proximal surface of the tibia for a tibial component of a prosthetic knee joint is disclosed. The arrangement includes a tibial and femoral stability gap preparation plate having a plurality of user operable height adjustable extension tabs that define a stability gap. Also disclosed is a stability gap guide drill plate adapted to act as a guide for a drill bit to drill a series of bore holes into the proximal surface of the tibia to a depth commensurate with the height adjustment of the user operable height adjustable extension tabs and a stability gap router plate adapted to allow a router to complete a final bone resection on the surface of the tibia to rout or cut away bone about each of the series of bore holes so as to provide a stable balanced complete angular movement between a tibial component and a femoral component of the prosthetic knee joint throughout an arc of motion from extension, mid-flexion and flexion. The instrument of WO2016065396 may involve a complicated surgical procedure requiring milling or burring of bone in order to arrive at a balanced knee.

SUMMARY OF THE INVENTION

The present invention aims to address at least one problem associated with instruments for balancing a knee joint.

According to the present invention there is provided an improved instrument as set forth in the appended claims. Other features of the invention will be apparent from the dependent claims, and the description which follows.

According to a first aspect of the present invention, there is provided an instrument for balancing a knee. The instrument may include a first plate, a second plate and a plurality of adjusters. The plurality of adjusters may be coupled to the first and second plates. The plurality of adjusters may be actuated to vary the gap between the first and second plates. Each adjuster of the plurality of adjusters may be coupled to the second plate by a joint having at least two degrees of freedom.

Preferably, consequential to actuation of an adjuster of the plurality of adjusters and the jointed coupling of each adjuster to the second plate, the second plate may rotate relative to each one of the joints.

Preferably, each adjuster of the plurality of adjusters may be mechanically actuated to vary the gap between the first and second plates along a respective adjustment axis. Each respective adjustment axis may be transverse to the first and second plates. Each joint coupling one of the adjusters to the second plate may include a center of rotation aligned with the respective adjustment axis. The second plate may be configured to rotate relative to each center of rotation consequential to the gap being varied along one of the adjustment axes.

Preferably, each joint coupling one of the adjusters to the second plate may include a center of rotation about which the second plate rotates with two degrees of freedom. Each center of rotation may be aligned with a respective adjustment axis that traverses the first and second plates. Mechanical actuation of one of the adjusters may vary the gap along its respective adjustment axis between the first plate and the joint coupling said adjuster to the second plate.

Preferably, the second plate may be configured to rotate about the center of rotation of each joint consequential to mechanical actuation of one of the adjusters and the coupling to the joint.

Preferably, when the gap is varied by one of the adjusters along its respective adjustment axis, the gap along the respective adjustment axis of the other adjusters of the plurality of adjusters may remain the same. The second plate may be configured to rotate relative each center of rotation consequential to the gap being varied along one of the adjustment axes.

Preferably, the plurality of adjusters may consist of three adjusters. The three adjusters may mechanically actuated to vary the gap along their respective adjustment axes. When viewed in plan, the points at which the respective adjustment axes traverse the first and second plates are coaxial. The points at which the respective adjustment axes traverse the first and second plates may form a triangular arrangement.

Preferably, each joint may include a first and a second pin joint. The first pin joint may provide the first degree of freedom and the second pin joint may provide the second degree of freedom. The second plate may be configured to rotate relative to first and second pin joints of each joint whilst an adjuster of the plurality of adjusters is mechanically actuated to vary the gap between the first and second plates.

Preferably, a top surface of the first plate may be arranged to face a bottom surface of the second plate. The plurality of adjusters may be arranged between the top and bottom surfaces.

Preferably, the plurality of adjusters may consist of three adjusters arranged in a triangular configuration.

Preferably, each adjuster of the plurality of adjusters may include a half-scissor jack, each half scissor jack comprising a pivot that is part of the joint. Each jack may include a bolt, a first coupling block, a second coupling block, a first lever arrangement, a second lever arrangement, a first hinge, a second hinge and a third hinge. The bolt may extend from a first end to a second end along a longitudinal axis. The bolt may have a center portion dividing the bolt into a first portion from the first end to the center portion and a second portion from the second end to center portion. The first portion may include an external left hand thread. The second portion may include an external right hand thread. One of the first or second ends may be configured to be engaged by an actuator for rotating the bolt. The first coupling block may be arranged on the first portion of the bolt. The first coupling block may include a channel having an internal thread configured to mate with the left hand thread of the first portion. The second coupling block may be arranged on the second portion of the bolt. The second coupling block may include a channel having an internal thread configured to mate with the right hand thread of the second portion. The first lever arrangement may extend from a first end to a second end. The second lever arrangement may extend from a first end to a second end. The first hinge may couple the first end of the first lever arrangement to the first coupling block. The second hinge may couple the first end of the second lever arrangement to the second coupling block. The third hinge may couple together the second ends of the first and second lever arrangement adjacent the center portion. The third hinge may form the pivot of the jack. Each adjuster may be configured such that actuation of the bolt by an actuator translates the first and second coupling blocks equally along the longitudinal axis relative to the center portion to thereby cause the distance between the first and second hinges to be varied equally relative to the center portion. Consequential to the distance of the first and second hinges being varied, the gap between the pivot and the center portion may be varied relative to the center portion in a direction transverse to the longitudinal axis in order to vary the gap between the first and second plates. Preferably, each jack may further include a fourth hinge associated with the third hinge. The third and fourth hinges may form the joint coupling each adjuster to the second plate to thereby provide the at least two degrees of freedom with which the second plate rotates relative to each one of the joints as the gap between at least one of the pivots of the plurality of adjusters is varied relative to the center portion. Preferably, the third and fourth hinges may include pin joints that are arranged transverse with respect to each other to provide the at least two degrees of freedom of the joint. Preferably, the third hinge may include a recess arranged to accommodate the center portion of the bolt. Preferably, the actuator may translate the first and second coupling blocks between an extended and a contracted arrangement. Preferably, in the extended arrangement, the center portion of the bolt is recessed into the third hinge. Preferably, in the extended arrangement, a first angle between the first hinge and third hinge relative to the longitudinal axis and a second angle between the second hinge and the third hinge relative to the longitudinal axis may be 49 degrees, and in the contracted arrangement the first and the second angle may be 6 degrees. Preferably, the height of the instrument may be approximately 15.5 mm in the extended positon and 8 mm in the contracted arrangement. Preferably, the left hand and right hand threads may have a square pattern. Preferably, the first lever arrangement comprises a first and a second lever arm, the second lever arrangement comprises a third lever arm and a fourth lever arm, and each lever arm extends from a first end to a second end. The first ends of the first and second lever arms may be coupled on opposed sides of the first coupling block to respective first and second hinge members forming the first hinge. The first ends of the third and fourth lever arms may be coupled on opposed sides of the second coupling block to respective third and fourth hinge members forming second hinge. The third hinge may include a yoke comprising a fifth hinge member on one side of a mid-portion and a sixth hinge member of an opposed side of the mid-portion, the second ends of the first and third lever arms are coupled together by the fifth hinge member and the second ends of the second and fourth lever arms are coupled together by the sixth hinge member. The mid-portion of the yoke is arranged to accommodate the center portion of the bolt.

Preferably, the height of the instrument may be varied between 8 mm and 15.5 mm.

Preferably, each of the first and second plates may include top and bottom surfaces connected by a wall. The top surface of the first plate and the bottom surface of the second plate may be arranged to face other. Each adjuster of the plurality of adjusters may be coupled at discrete locations to the top surface of the first plate and the bottom surface of the second plate and space those surfaces apart along a respective adjustment axis that traverses the first and second plates. Each joint may couple one of the adjusters of the plurality of adjusters to the bottom surface of the second plate in alignment with its respective adjustment axis. The joint may enable the second plate to rotate about first and second axes that extend orthogonally with respect to each other and with respect to its respective adjustment axis. When one of the adjusters is actuated, the gap between the bottom surface of the second plate may be varied relative to the top surface of the first plate and consequentially the bottom surface rotates about the first and second axes of each joint.

Preferably, the first plate lies substantially in a first plane. The second plate lies substantially in a second plane. The plurality of adjusters comprises three adjusters. The three adjusters are arranged in between the first and second plates in a triangular arrangement relative to the first and second planes.

Preferably, the second plate may include a connector to receive and hold an outrigger.

Preferably, the second plate comprises at least one recess to accommodate at least one joint coupling one of the adjusters of the plurality of adjusters to the second plate. Preferably, the recess is a cut through in the second plate.

Preferably, the first plate may be configured to be placed on a tibial side of a knee.

The second plate may be arranged relative to the first plate to be engaged with a femoral side of the knee by actuation of at least one of the plurality of adjusters.

According to a second aspect of the present invention, there is provided a kit including the instrument of the first aspect claim and an outrigger. The outrigger may include a body. The body may include a connection component. The connection component may be configured to be received and held by the connector. The body may include a slot arranged to align a blade of a surgical saw with a portion of a knee to be cut.

According to a third aspect of the present invention, there is provided a method of balancing a knee including a first and a second bone. The first bone may be a tibia and the second bone may be a femur.

Preferably, the method may include:
performing an initial resection of a first bone of the knee;
inserting an instrument into the gap between the first bone and the second bone, the instrument comprising:
  a first plate,
  a second plate, and
  a plurality of adjusters coupled to the first and second plates and actuatable to vary the gap between the first and second plates, each adjuster of the plurality of adjusters being coupled to the second plate by a joint having at least two degrees of freedom;
configuring the knee for adjustment of the instrument;
adjusting the instrument to apply a distraction force to the knee joint;
assessing a balance of a knee joint; and
identifying an optimal knee balance.

Preferably, the method further includes, after an optimal knee balance has been identified, coupling an outrigger to the instrument. The outrigger may be arranged to transfer a balance plane to a resection plane on one of the first or second bones.

Preferably, the method further includes coupling a cutting block to the outrigger, pinning the coupling block to one of the first or second bones, and resecting the first or second bone to which the cutting block is attached.

According to a fourth aspect of the present invention, there is provided a method of fabricating an instrument. The method may include:
providing a first plate comprising a plurality of stations, each station configured to receive an adjuster;
locating an adjuster of a plurality of adjusters in each of the plurality of stations;
securing each adjuster of the plurality of adjusters in position;
positioning a second plate relative to the plurality of adjusters; and
coupling the second plate to each adjuster of the plurality of adjusters.

The second plate may be hingedly coupled to each adjuster by a joint having at least two degrees of freedom.

BRIEF DESCRIPTION OF THE DRAWINGS

The foregoing summary, as well as the following detailed description, is better understood when read in conjunction with the appended drawings. There is shown in the drawings example embodiments, in which like reference numerals correspond to like reference numerals throughout. The present disclosure is not limited to the specific embodiments and methods disclosed, and reference is made to the claims for that purpose. The drawings are not intended to be drawn to scale. For purposes of clarity, not every component may be labeled in every drawing. In the drawings:

DETAILED DESCRIPTION OF THE INVENTION

Figure 1:
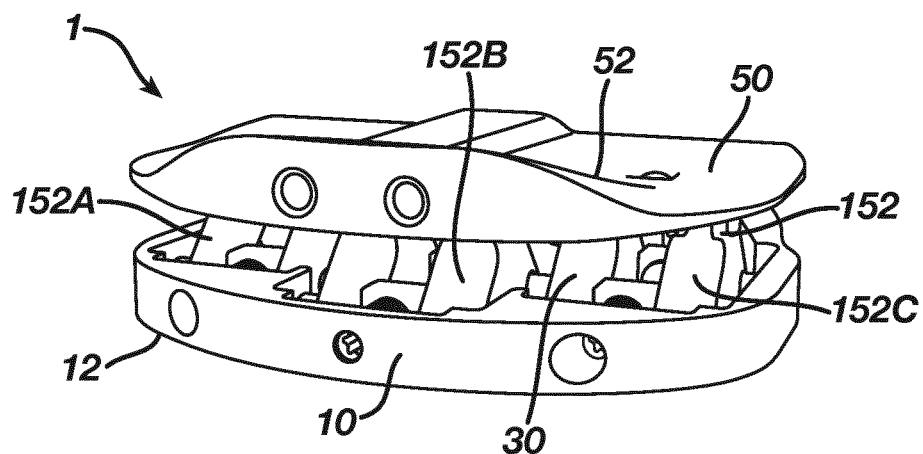
FIG. 1 shows a perspective view of an instrument of an embodiment of the present invention.

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to an instrument, assembly, kit and method for balancing a patient's knee during a knee replacement procedure. Knee replacement procedures, also known as knee arthroplasty, include procedures to totally replace a knee, partially or unilaterally replace part of a knee, and to revise an already replaced knee. The embodiments of the present invention have applicability to all types of knee replacement surgery whether described herein or otherwise.

During surgery, a medical practitioner operates to replace damaged parts of a patient's knee with an appropriate artificial joint. Typically, the medical practitioner will perform some of the following steps to replace a knee:

The medical practitioner may perform a series of incisions and cuts to open up and prepare a knee joint for the replacement procedure;

A bone saw may be used to remove damaged areas of the knee, typically from the articulating parts of the knee joint such as the distal end of the femur and the proximal end of the tibia.

The medical practitioner may reshape the bones as necessary to fit a knee replacement prosthesis. Typically, the cuts are made with a degree of precision, and the medical practitioner may use, for example, jigs and cutting blocks and computer assistance in the performance of the cuts.

In certain procedures, a surgeon may resurface and replace the side of the kneecap, also known as the patella, that contacts and slides relative to the femur and tibia.

After initial cuts are performed, typically, trail implants are inserted and a medical practitioner may assess the knee joint to evaluate the final prosthesis components to implant.

Finally, the knee prosthesis is implanted and, after performing tests to evaluate the knee replacement, the medical practitioner closes the knee joint.

The embodiments of the present invention are used to assist with the medical practitioner in the performance of cuts to reshape a patient's knee for receiving a knee replacement prosthesis. In an embodiment, the invention is an instrument that allows distraction of the knee joint and subsequent identification of a plane perpendicular to the kinematic alignment of the knee, and final tibial resection parallel to that plane.

To achieve this and other purposes, an instrument according to the present invention including a first plate coupled to a second plate by an adjustment arrangement is disclosed. The instrument either by itself or in connection with a jig or jigs allows a medical practitioner to vary the gap between the first and second plates in three dimensions to facilitate assessment by a medical practitioner of the balance of the knee joint. The instrument facilitates evaluation of the balance of the knee joint and supports decision making by the medical practitioner of where to resect the bones making up the knee joint relative to the kinematic alignment of the knee.

The instrument enables assessment of full three-dimensional planer balance of the knee joint, with reference to the soft tissue tension and kinematic alignment of the knee. The instrument 1 allows the balance to be assessed without specific reference to varus or valgus of a knee. The instrument 1 can be configured to allow for maximum opening height to accommodate maximum bearing thicknesses of known knee replacement systems. For example, the maximum opening height of the instrument for the DePuy Synthes® Attune® primary knee system is 18 mm.

FIG. 1 shows an instrument 1 according to an embodiment of the present invention.

The instrument 1 has a first plate 10 coupled to a second plate 50 by an adjustment assembly 150. The first plate has a generally planar bottom surface 12 for positioning on a first bone (not shown), such as a tibia. The second plate 50 has an undulating top surface 52 for engagement by a second bone (not shown), such as a femur. The adjustment assembly 150 is arranged between the first and second plates 10, 50 to vary the distance and angulation of the plates 10, 50 relative to each other. Variation of the distance and angulation between the first and second plates 10, 50 consequentially varies the distance between the first and second bone and the angle at which bone axes (not shown) articulate relative to each other.

The adjustment assembly 150 includes a plurality of adjusters 152A, 152B, 152C arranged between the first and second plates 10, 50. In the embodiment shown by FIG. 1, the adjustment assembly 150 comprises three adjusters 152A, 152B, 152C. The plurality of adjusters 152A, 152B, 152C are coupled to the first and second plates 10, 50. The plurality of adjusters 152A, 152B, 152C are actuatable to vary the gap between the first and second plates 10, 50. Separately, the plurality of adjusters 152A, 152B, 152C are coupled to the second plate 50 with at least two degrees of freedom to enable variance of the angulation between the first and second plates 10, 50.

The instrument 1 is dimensioned such that it fits completely inside the joint space of a patient's knee. Once inserted, the instrument does not protrude anteriorly out of the joint space. In this way, the instrument 1 does not interfere with patella ligament of a patient's knee. The instrument 1 allows balance at any point throughout the full range of flexion and extension to be assessed, including full extension and full flexion or at any degree of flexion in between.

Figure 12:
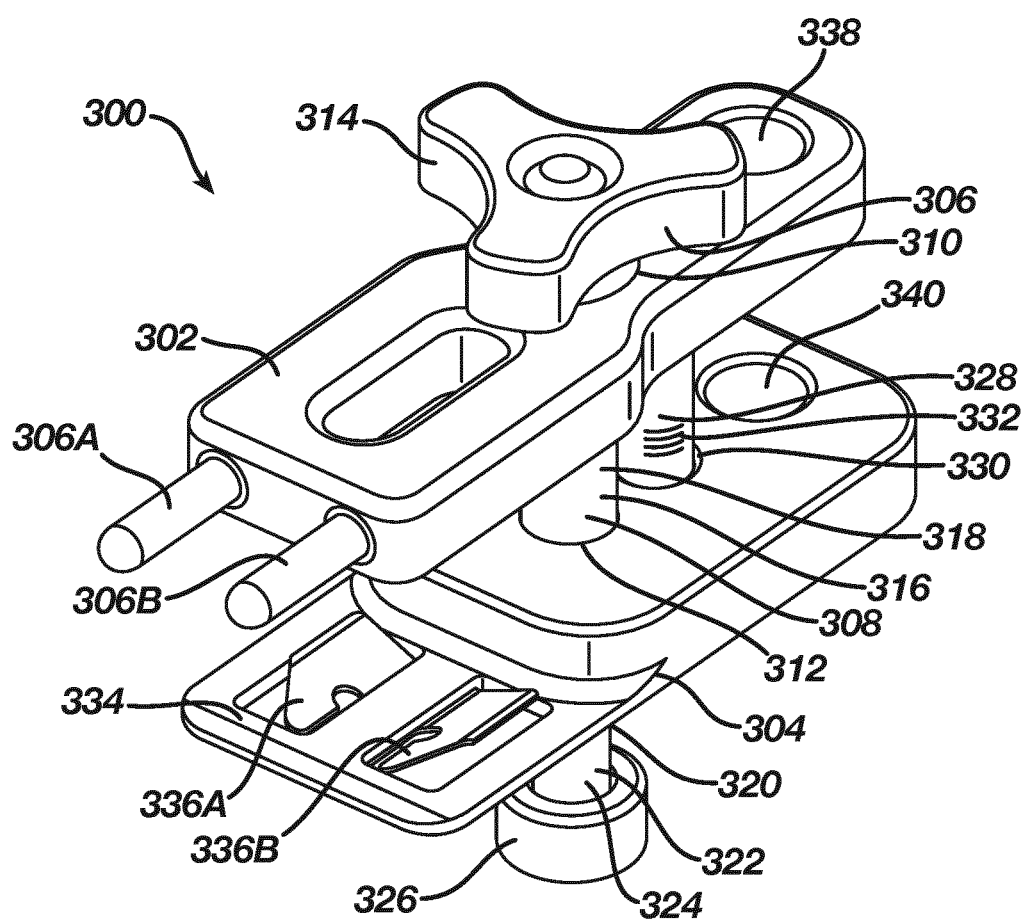
FIG. 12 shows a perspective view of an outrigger, or resection guide, of an embodiment of the present invention.
Figure 13:
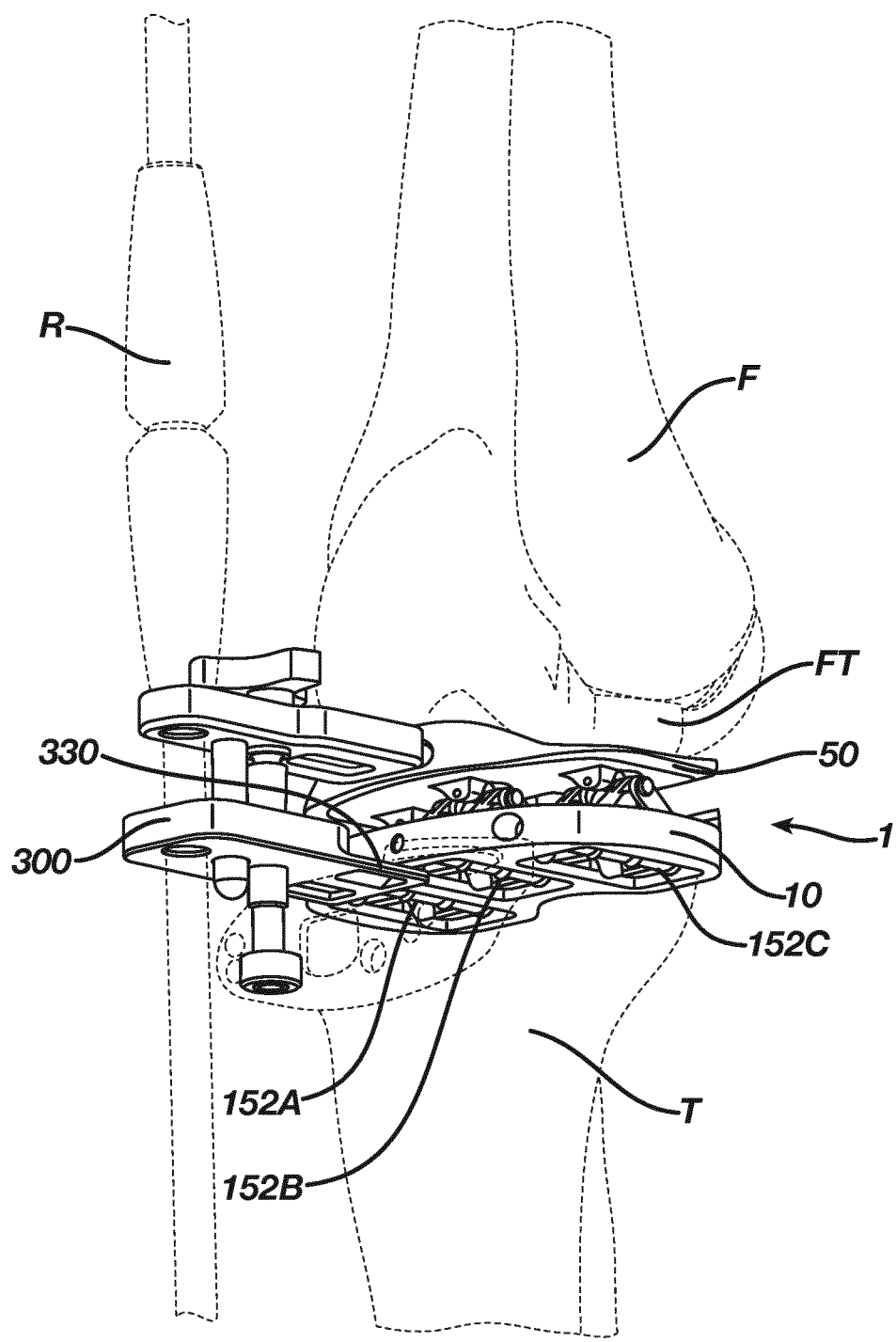
FIG. 13 shows a perspective view of a knee joint with the instrument of FIG. 1, the outrigger of FIG. 12 and an alignment rod in situ.

The invention also includes an outrigger 300, as shown by FIG. 12. The outrigger 300 can be coupled to a cutting block (not shown) to enable an operator of the instrument 1 to resect a patient's tibia or femur. The outrigger 300 is configured to receive a guide rod R, as shown by FIG. 13, to enable a medical practitioner to assess alignment of the tibia and femur.

Figure 2:
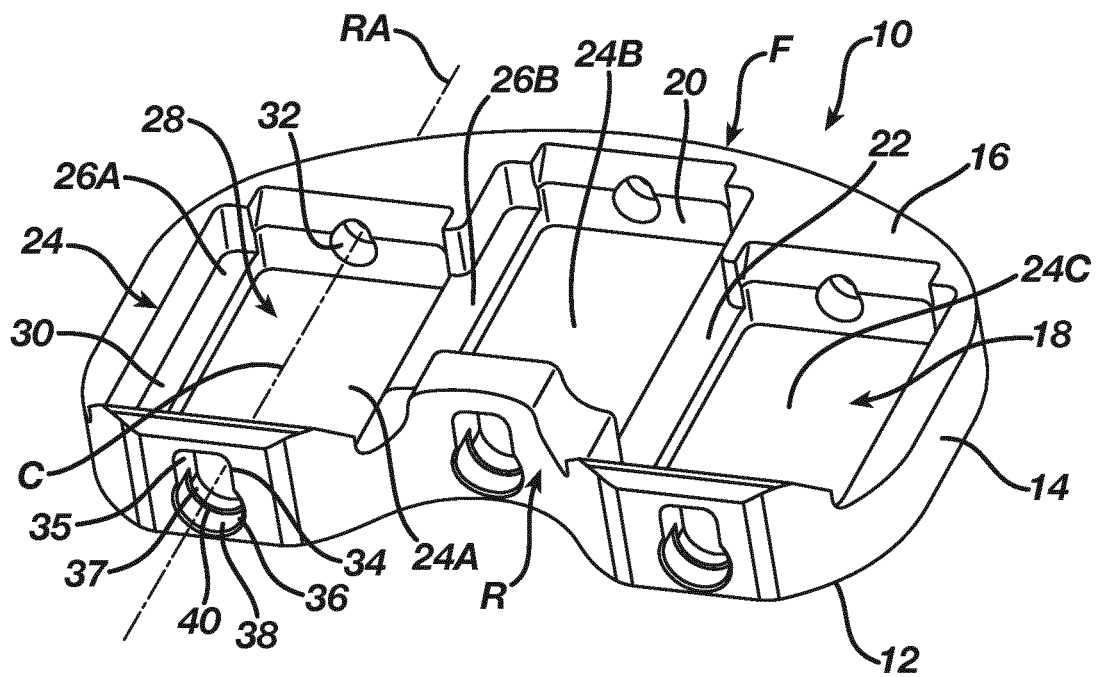
FIG. 2 shows a perspective view of a first plate of the instrument of FIG. 1.

Referring to FIG. 2, the first plate 10 has a sidewall 14 separating the bottom surface 12 from a top surface 16. The sidewall 14 defines a profile of the first plate 10. The profile is selected to correspond to the shape of the proximal end of a tibia, i.e. the tibial plateau. The profile of the first plate 10 could be described as kidney shaped, but as a person skilled in the art would understand the invention is not limited to kidney shaped first plates and other shapes are of course possible.

The first plate 10 comprises a recess 18 in the top surface 16. The recess 18 is defined by an internal sidewall 20 and an internal bottom surface 22. The internal sidewall 20 defines a series of stations 24A, 24B, 24C. Each station 24A, 24B and 24C is shaped to accommodate an adjuster 152 of the plurality of adjusters 152A, 152B, 152C. Each station 24A, 24B and 24C has the same set of features for receiving an adjuster 152 and, for simplicity in the following few paragraphs, a single station 24 will be described. As a person skilled in the art would understand, the description for a single station 24 applies to each of the series of stations 24A, 24B, 24C.

The station 24 has a pair of rails 26A, 26B either side of a cavity 28 that passes through the internal bottom surface 22 to bottom surface 12. Each rail of the pair of rails 26A, 26B runs parallel to each other on either side of the cavity 28. Each rail of the pair of rails 26A, 26B has a sliding surface 30. The sliding surface 30 of the each of the pairs of rails 26A, 26B is defined by the planar internal bottom surface 22. The sliding surfaces 30 of the pair of rails 26A, 26B is arranged to receive a portion of one of the adjusters 152 and, as will be described in more detail below, supports that portion as it slides relative to an axis RA passing through a center C of the station 24.

The station 24 has a first channel 32 and second channel 34. The first channel 32 is arranged at the front F of the instrument 1 and is defined by openings in the sidewall 14 and internal sidewall 20 connected by a tunnel. The first channel 32 has a circular cross-section with a diameter of 3.6 mm. The second channel 34 is arranged at the rear R of the instrument 1 and is defined by openings in the sidewall 14 and internal sidewall 20 connected by a tunnel. The first channel 32 and second channel 34 are aligned with each other along the axis RA that passes through the channels 32, 34.

The second channel 34 is a slot. The second channel has a first portion 35 arranged in the vicinity of, or adjacent to, the top surface 16 and a second portion 36 in the vicinity of, or adjacent to, the bottom surface 12. The first portion 35 is shaped to receive a part of an adjuster 152 as it is assembled into a station 24. In the exemplary embodiment, the first portion is substantially square in cross-section and has a width of 4.5 mm. The second portion 36 is shaped to receive a plug 280, shown in FIG. 6, of an adjuster 150 therethrough for securing an adjuster 152 to the first plate 10. The second portion 36 has a substantially circular cross-section.

The second portion 36 has a first region 37 leading to an increased diameter second region 38. The transition between the first and second regions 37, 38 defines a shoulder 40. The first region 37 leads part way into the second channel 34 from the inner sidewall 20 to the shoulder 40 and a second region 38 leads part way from the outer side wall 14 into the second channel 34 to the shoulder 40. The diameter of the second region 38 is greater than the diameter of the first region 37. The shoulder 40 is formed due to the difference in diameter between the first and second regions 37, 38. The diameter of the first region 37 is 4.5 mm and the diameter of the second region 38 is 5.2 mm. As a person of skill in the art would understand other diameters are of course possible.

Figure 3A:
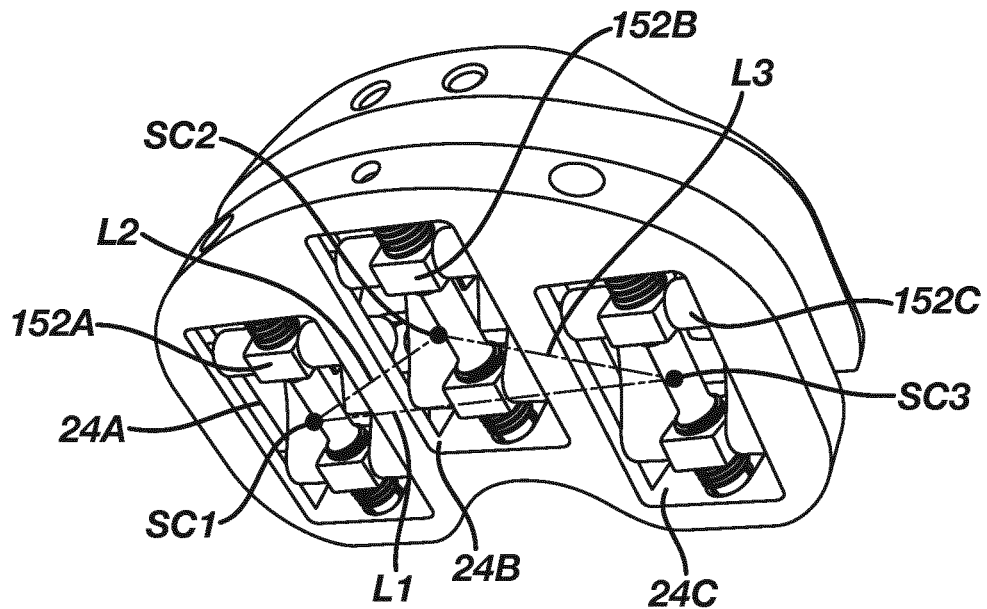
FIG. 3A shows a perspective view of the base of the instrument of FIG. 1.

Referring now to FIG. 3A, when viewed in plan, the series of stations 24A, 24B and 24C are spaced apart from each other in a triangular arrangement. As will be described in more detail below, when the instrument is assembled and used, the triangular arrangement arranges the adjusters 152A, 152B, 152C in a triangular relationship. In the triangular relationship, the adjusters 152A, 152B, 152C may vary the distance and angulation between the first and second plates 10, 50 and consequentially vary the distance between the first and second bones (not shown) and the angle at which bone axes (not shown) articulate relative to each other.

Each station 24A, 24B, 24C have respective centers SC1, SC2, SC3 that correspond to the central points of the adjusters 152A, 152B, 152C. The centers SC1, SC2, SC3 form a triangular arrangement. A line L1 drawn between the centers SC1, SC3 form the base of the triangle. Line L2 drawn from center SC1 to SC2 and L3 drawn from center SC3 to SC2 form the sides of the triangle. As can be seen lines L1, L2 and L3 form an isosceles triangle. The separation between the centers SC1 and SC3, i.e. the length of the line L1, is 38 mm. The separation between the centers SC1 and SC2, i.e. the length of the line L2, is 20.8 mm. The separation between the centers SC3 and SC2, i.e. the length of the line L3, is 20.8 mm. In this exemplary embodiment, the lines L2 and L3 are the same length. As a person of skill in the art would understand other lengths and separation distances are of course possible.

Figure 3B:
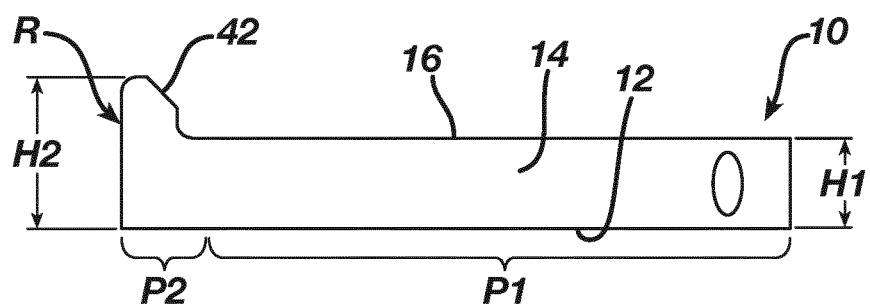
FIG. 3B shows a plan view of the base of the first plate of FIG. 2.

Referring now to FIG. 3B, the first plate 10 has a major portion P1 and a minor portion P2. The minor portion P2 is located adjacent the rear R of the first plate 10. The major portion P2 runs from the minor portion P1 to the front F of the first plate 10. In the major portion P1, the top and bottom surfaces 16, 12 are both planar and lie in planes lying parallel to each other, the planes spaced apart by the sidewall 14. In the minor portion P2, the top surface 16 deviates from the plane to form a ramp 42. The ramp 42 supports alignment of the second plate 50 as the gap and angulation between the first and second plates 10, 50 is varied. In the minor portion P2, the bottom surface 12 lies in the same plane as it lies in the major portion P1.

Figure 3C:
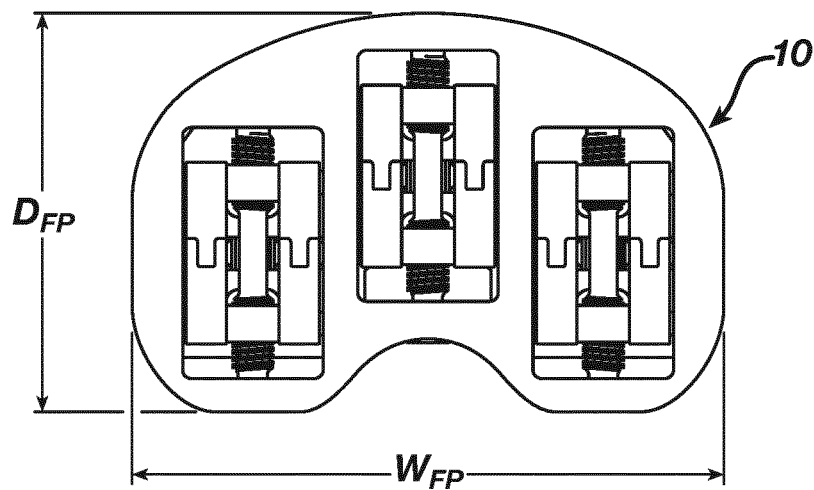
FIG. 3C shows a side view of the first plate of FIG. 2.

Referring now to FIGS. 3B and 3C, the first plate 10 has a maximum width $W_{FP}$ and a maximum depth $D_{FP}$. A major portion P1 of the first plate 10 has a height H1. A minor portion P2 of the first plate 10 has a maximum height H2. In the exemplary embodiment shown, the width $W_{FP}$ is, for example, 43.75 mm. The depth $D_{FP}$ is, for example, 64.00 mm. The height H1 is, for example, 6 mm. The maximum height H2 is, for example, 10 mm. A person skilled in the art would understand the widths, depths and heights are exemplary and other dimensions are possible.

Figure 4A:
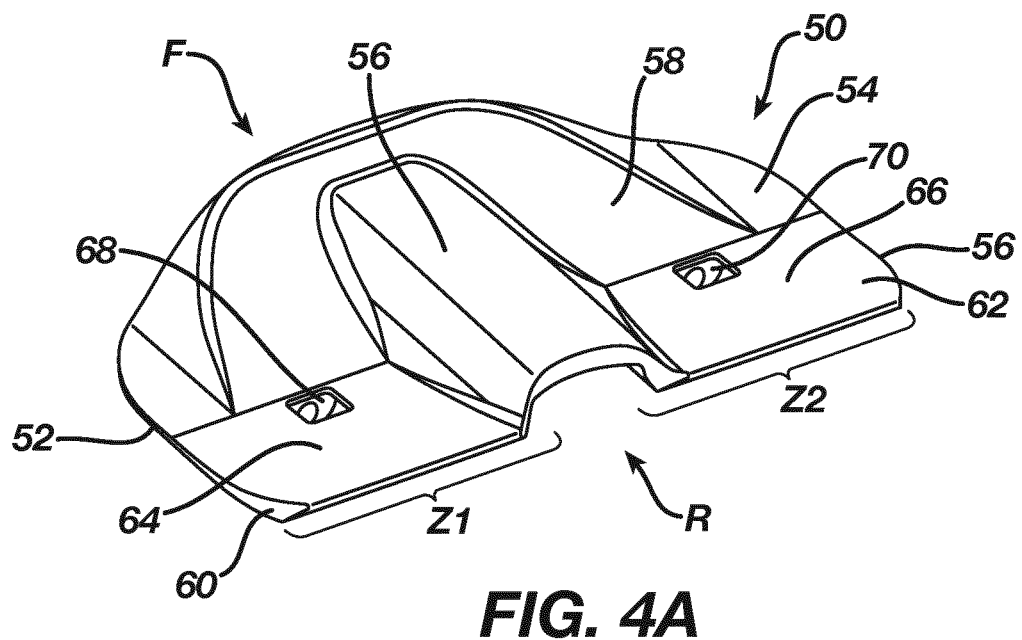
FIG. 4A shows a perspective view of an articulation surface of a second plate of the instrument of FIG. 1.

FIG. 4A shows the second plate 50. The second plate 50 has a bottom surface 52 and a top surface 54. An edge 56 defines a profile of the second plate 10. The profile is selected to correspond to the shape of a distal end of a femur. When viewed in plan, the profile of the second plate 50 could be described as D-shaped, but as a person skilled in the art would understand the invention is not limited to D-shaped second plates and other shapes are of course possible.

The top surface 54 has an undulating surface. The surface 54 is divided into two zones Z1, Z2 by a ridge 56. Each of the zones Z1, Z2 is configured receive a condyle of the femoral condyles at the distal end of a femur (not shown). A slope 58 is arranged at the front F of the second plate 50. The slope 58 is split by the ridge 56 as it leads into the zones Z1, Z2. At the rear R of the second plate 50 each zone Z1, Z2 ends in a respective ramp 60, 62.

The slope 58 curves into the zone Z1 that continues into the ramp 60 and defines a first articulating surface 64. The zone Z2 is a mirror image of the zone Z1, with the ridge 56 defining a central point about which Z2 is mirrored with respect to Z1. Similarly to zone Z1, the slope 58 curves also into the zone Z2 and continues into the ramp 62 to define a second articulating surface 66. The curvature of the surfaces 64, 66 is chosen to support articulation of the femur (not shown) as the medical practitioner uses the instrument 1 to check the balance of a patient's knee (not shown).

The second plate 50 has apertures 68, 70 to accommodate a portion of the adjusters 152A, 152C. The apertures 68, 70 are located substantially adjacent the nadir of the curve of articulating surfaces 64, 66. The apertures 68, 70 pass through the top surface 54 to the bottom surface 52.

Figure 4B:
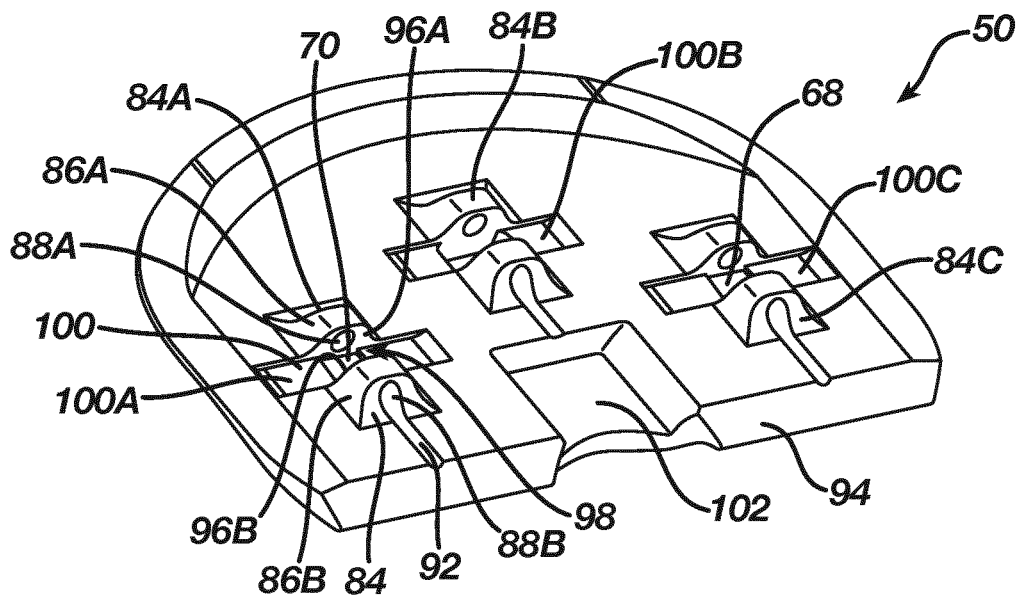
FIG. 4B shows a perspective view of a joint coupling surface of the second plate of FIG. 4A.

Referring now to FIG. 4B, the second plate 50 has a series of hinge members 84A, 84B, 84C. The hinge members 84A, 84B, 84C are for rotatably coupling the plurality of adjusters 152A, 152B 152C to the second plate 50. Each hinge members 84A, 84B, 84C has the same set of features and, for simplicity in the following few paragraphs, a hinge member 84 will be described. As a person skilled in the art would understand, the description for the hinge member 84 applies to each of the hinge members 84A, 84B, 84C.

The hinge member 84 has a pair of protrusions, or knuckles, 86A, 86B. Each protrusion 86A, 86B has a pair of coaxial channels 88A, 88B for receiving a pin 90, as shown in FIG. 7C. The pin 90 rotatably couples an adjuster 152 to the second plate 50. Referring back to FIG. 4B, a groove 92 is formed in the bottom surface 54 of the second plate 50. The groove 92 leads into the channels 88A, 88B from a rear edge 94 of the second plate 50. The groove 92 facilitates positioning of the pin 90 in the channels 88A, 88B.

The rear edge 94 of the bottom surface 54 defines a ramp. The rear edge 94 is angled similarly to ramp 36 of the first plate 10. The correspondence of rear edge 94 to ramp 36 supports alignment for the first and second plates 10, 50 as the gap and angulation between the plates is varied.

The protrusions 86A and 86B each have opposed faces 96A, 96B arranged to face each other. The faces 96A, 96B are spaced apart by a gap 98. In the exemplary embodiment shown by FIG. 4B, the length of the gap 98 is 3.5 mm and is chosen to receive a part of the adjuster 152 that is to be coupled to the second plate 50.

Figure 8A:
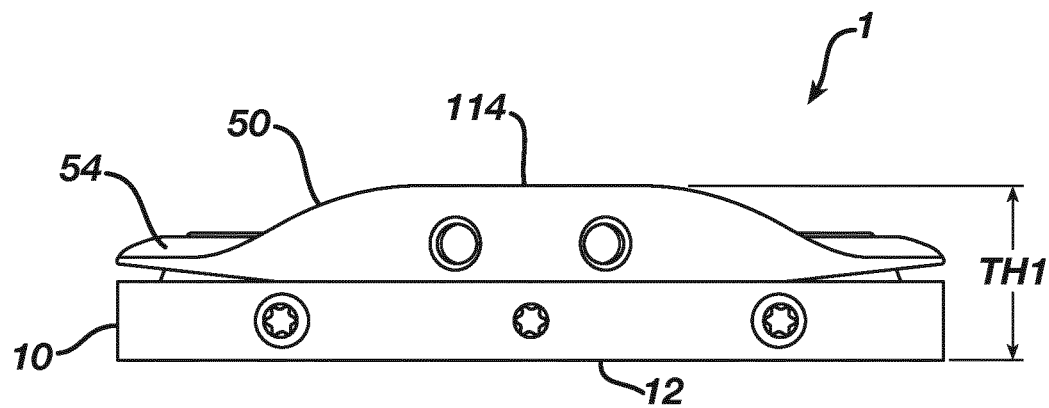
FIGS. 8A-8E show a series of views of the instrument of FIG. 1 in an insertion configuration.

In the bottom surface 54, a recess 100 is formed. The recess 100 is provided to accommodate the part of the adjuster 152. Part of the recess 100 is arranged to traverse the gap 98. The recess 100 is provided to ensure that the instrument 1 in its insertion configuration as shown by FIG. 8A has a low profile. The low profile facilitates insertion of the instrument 1 into the knee joint during a surgical procedure.

The recesses 98A, 98C of each of hinge members 84A and 84C correspond with the apertures 68 and 70. The apertures 68, 70 are provided to accommodate a part of the adjuster 152 and provide a low profile for the instrument 1.

The recess 100B of the hinge member 84B is formed in a region of the second plate 50 aligned with the ridge 56. In the exemplary embodiment shown, due to the ridge 56, an aperture is not necessary to accommodate a part of the adjuster 152 and provide a low profile for the instrument 1. However, as a person of skill in the art would understand, an aperture could be provided.

The gap 98 of each hinge member 84A, 84B, 84C defines a center of the hinge. Each center is located equidistant between respective opposed faces 96A, 96B. The centers form a triangular arrangement that, when the instrument 1 is assembled, corresponds to the triangular arrangement formed by centers SC1, SC2, SC3 of the first plate 10. As a person of skill in the art would understand, the centers are dimensionally separated in the same manner described in relation to lines L1, L2 and L3 drawn between centers SC1, SC2, SC3 on FIG. 3A.

Referring again to FIG. 4B, the bottom surface 54 features a notch 102. The notch 102 is located and dimensioned to accommodate a portion of the top surface 16 of the first plate 10 that houses the second channel 34 of the station 24B. Similarly to the recesses 100A, 100B, 100C the notch 102 is provided to ensure that the instrument 1 in its insertion configuration as shown by FIGS. 8A-8E has a low profile.

Figure 4C:
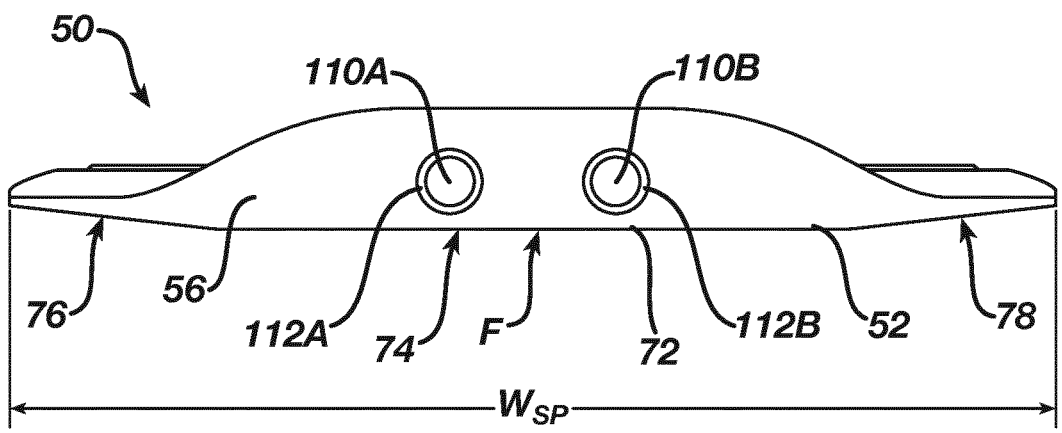
FIG. 4C shows a front or anterior view of the second plate of FIG. 4A

Referring now to FIG. 4C, the top plate 50 has first and second outrigger channels 110A, 110B defined in the edge 56. The outrigger channels 110A, 110B are defined in the front F of the second plate 50. The outrigger channels 110A, 110B include first and second outrigger apertures 112A, 112B that are defined in the edge 56. The apertures 112A, 112B are spaced apart and, when the second plate 50 is viewed from the front as shown in FIG. 4C, the apertures 112A, 112B are equidistant from the midpoint of the second plate 50. The apertures 112A, 112B are chamfered as they lead into the channel 110A, 110B to facilitate easy insertion of the outrigger 300 into the channels 110A, 110B. In the exemplary embodiment depicted by FIG. 4C, the channels 110A, 110B have a diameter of 3.0 mm for receiving and retaining by friction fit the outrigger 300. In the exemplary embodiment depicted by FIG. 4C, the channels 110A, 110B have a length of 10.6 mm and have a closed end. In the exemplary embodiment depicted by FIG. 4C, the channels 110A, 110B are spaced apart by a distance of 10 mm. As a person of skill in the art would understand, these dimensions and distance are merely exemplary and other distances and dimensions are of course possible.

Referring to FIG. 4C, the bottom surface 52 has a contact surface 72 configured to abut the top surface 16 of the first plate 10. As can be shown by FIG. 4C, contact surface 72 has a central area 74 either side of which are angled areas 76, 78 that are angled from the central area towards side edges 80, 82 of the second plate 50. The angle at which the angled areas 76, 78 deviate from the planar contact surface 72 is 6.6 degrees to accommodate variation of the angulation of the second plate 50 relative to the first plate 10 in use. As a person of skill in the art would understand, this angle is merely exemplary and other angles are of course possible.

Figure 4D:
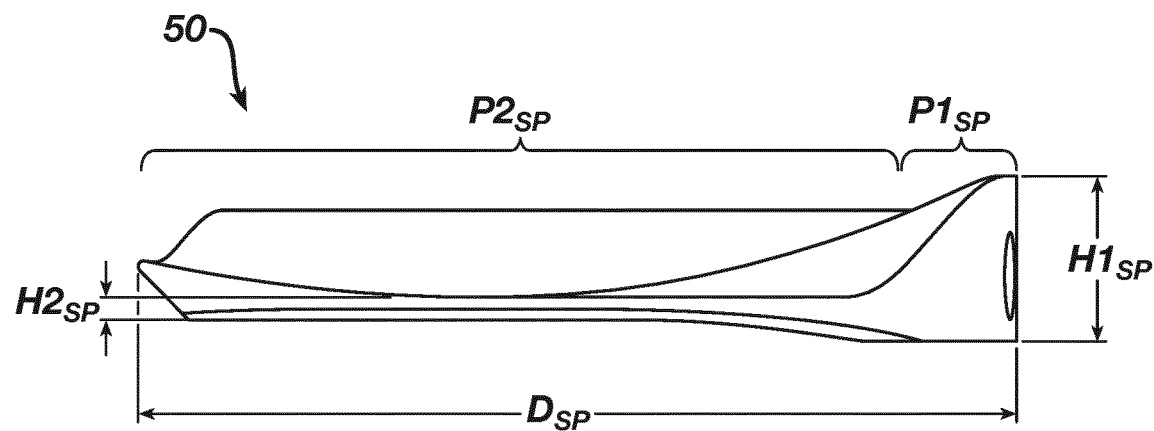
FIG. 4D shows a side view of the second plate of FIG. 4A.

Referring to FIGS. 4C and 4D, the second plate 50 has a maximum width $W_{SP}$ and a maximum depth $D_{SP}$. A major portion $P_{SP}$ of the second plate 50 has a height $H1_{SP}$. A minor portion $P2_{SP}$ of the second plate 50 has a curvature defined by both the top surface 52 and the bottom surface 54. Both curvatures have a nadir. The distance between the nadir defines a distance which is a minimum height $H2_{SP}$. The width $W_{SP}$ is for example 64 mm. The depth $D_{SP}$ is for example 40.1 mm. The maximum height $H1_{SP}$ is 5 mm. The maximum height $H2_{SP}$ is 1 mm. A person skilled in the art would understand the widths, depths and heights are exemplary and other dimensions are possible.

Figure 5A:
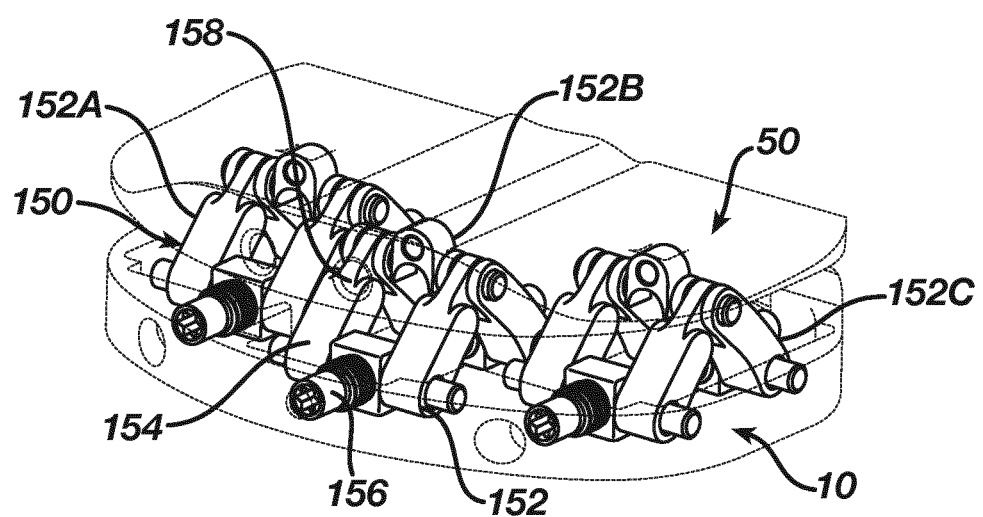
FIG. 5A shows a perspective view of the instrument of FIG. 1 showing the first and second plates ghosted allowing an adjustment assembly of the instrument to be seen.
Figure 5B:
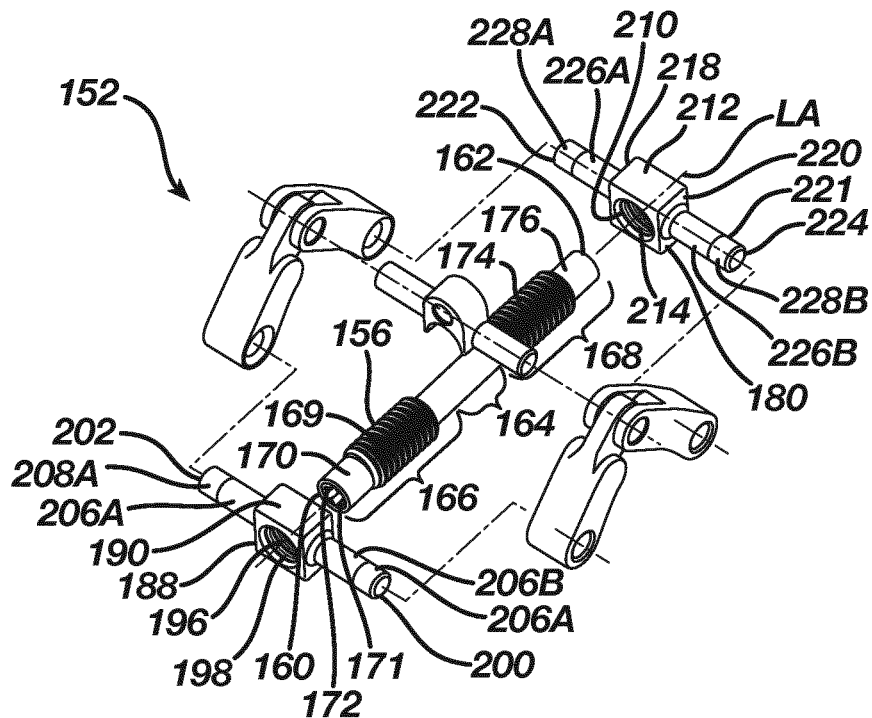
FIG. 5B shows an exploded view of an adjuster of the adjustment assembly of FIG. 5A.
Figure 5C:
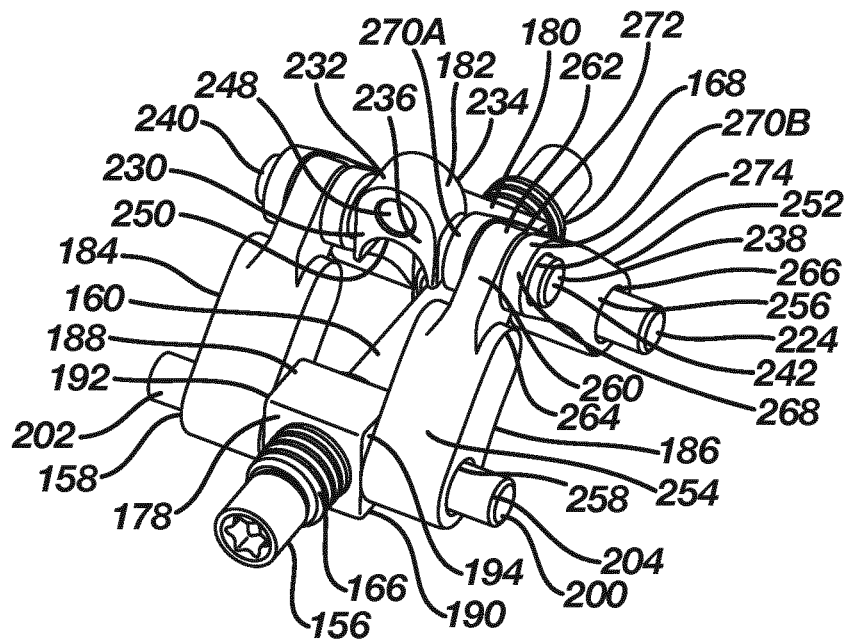
FIG. 5C shows a perspective, assembled view of the adjuster of FIG. 5B.

FIGS. 5A-5C show the adjustment assembly 150 arranged between the first and second plates 10, 50. In the exemplary embodiment depicted in FIG. 5A, the adjustment assembly 150 has three adjusters 152A, 152B, 152C. Each adjuster 152A, 152B, 152C is positioned in a station 24A, 24B and 24C to adjust the gap between the first and second plates 10, 50.

Each adjuster 152A, 152B, 152C has the same set of features and, for simplicity, in the following few paragraphs a single adjuster 152 will be described. As a person skilled in the art would understand, the description for a single adjuster 152 applies to each of the plurality of adjusters 152A, 152B, 152C.

The adjuster 152 a mechanism 154 to adjust the gap between first and second plates 10, 50. The mechanism 154 is a jack mechanism that includes a half-scissor jack. The mechanism 154 has a jack assembly that includes a bolt 156 and a lever arm assembly 158. In the exemplary embodiment depicted in FIG. 5A, the adjustment assembly 150 includes 3 jack mechanisms 154 arranged to provide a planer reference with optimal planer stability.

Referring to FIG. 5B, it can be seen that the bolt 156 extends from a first end 160 to a second end 162 along a longitudinal axis LA. The bolt 156 has a center portion 164 dividing the bolt 156 into a first portion 166 from the first end 160 to the center portion 164. The bolt 156 has a second portion 168 from the second end 162 to center portion 164.

The first portion 166 has a threaded region 169 adjacent the center portion 164 that extends to a non-threaded region 170. The non-threaded region 170 extends from the threaded region 169 to the first end 160. The threaded region 169 features an external left hand thread. The non-threaded region 170 is shaped and dimensioned to be received and rotatably held in the first channel 32 of the first plate 10. The non-threaded region 170 has a circular cross section with a diameter of 3.5 mm. The first end 160 includes a recess 171. The recess 171 includes an internal sidewall 172 shaped to receive an actuator (not shown) and transmit a torque from the actuator to the bolt 156. The sidewall 172 is shaped to receive a star-shaped driving mechanism, for example a Torx® drive to enable the transmission of high torques to the bolt 156.

The second portion 168 has a threaded region 174 adjacent the center portion 164 that extends to a non-threaded region 176. The threaded region 174 features an external right hand thread. The non-threaded region 176 extends from the threaded region 174 to the second end 162. The non-threaded region 176 is shaped and dimensioned to be received in the second channel 34 of the first plate 10. The non-threaded region 176 has a circular cross section with a diameter of 3.1 mm.

Referring now to FIG. 5C, the lever arm assembly 158 has a first coupling block 178, a second coupling block 180, a third coupling block 182, a first lever arm 184 and a second lever arm 186.

the first coupling block 178 includes a body 188 having a sidewall 190. The sidewall 190 spaces apart opposed faces 192, 194 of the body 188 and has a width of 5.6 mm. In the exemplary embodiment shown, the body 188 is cuboid in shape and the sidewall 190 has a square cross-section.

Referring back to FIG. 5B, the body 188 has a channel 196. The channel 196 is surrounded by the sidewall 190. The channel 196 has an internal thread 198. The internal thread 198 is a left-hand thread and is configured to mate with the left-hand thread of the threaded region 170 of the first portion 166 of the bolt 156.

The first coupling block 178 has a first hinge coupling 200 for coupling the first and second pairs of lever arms 184, 186 to the first coupling block 178. The first hinge coupling 200 includes a first pin 202 and a second pin 204. The first and second pins 202, 204 extend from opposed sides of the body 188 from the sidewall 190. Each of the pins 202, 204 are cylindrical in shape and have a diameter of 2.5 mm. Each pin 202, 204 has a lever holding region 206A, 206B and a rail bearing region 208. Each lever holding region 206 extends from adjacent the body 188 to rail bearing region 208. Each rail bearing region 208 extends from the lever holding region 206 to the end of the pin. Each pin 202, 204 is 7 mm in length.

The second coupling block 180 is substantially similar to the first coupling block 178.

The main difference between the second coupling block 180 and the first coupling block 178 is that a channel 210 formed within a body 212 of the second coupling block 180 has an internal thread 214 of opposite handedness to the internal thread 198 of the first coupling block 178. The internal thread 214 of the second coupling block 180 is a right-hand thread and is configured to mate with the right-hand thread of the threaded region 174 of the second portion 168 of the bolt 156.

The body 212 has a sidewall 216 surrounding and defining the channel 210. The sidewall 216 spaces apart opposed faces 218, 220 of the body 212 and has a width of 5.6 mm. In the exemplary embodiment shown, the body 212 is cuboid in shape and the sidewall 216 has a square cross-section.

The second coupling block 180 has a second hinge coupling 221 for coupling the first and second pairs of lever arms 184, 186 to the second coupling block 180. The second hinge coupling 220 includes a third pin 222 and a fourth pin 224. The third and fourth pins 222, 224 extend from either side of the body 212 from the sidewall 216. Each of the pins 222, 224 are cylindrical in shape and have a diameter of 2.5 mm. Each pin 222, 224 has a lever holding region 226A, 226B and a rail bearing region 228A, 228B. Each lever holding region 226A, 226B extends from adjacent the body 212 to the rail bearing region 228A, 228B. Each rail bearing region 228A, 228B extends from the lever holding region 226A, 228B to the end of the pin. Each pin 222, 224 is 7 mm in length.

Referring again to FIG. 5C, the third coupling block 182 includes a body 230 having a sidewall 232. The sidewall 232 spaces apart opposed faces 234, 236 of the body 230 and has a width of 3.3 mm. The third coupling block 182 has a third hinge coupling 238 for coupling the first and second pairs of lever arms 184, 186 to the third coupling block 182. The third hinge coupling 238 includes a fifth pin 240 and a sixth pin 242. The fifth and sixth pins 240, 242 extend from opposed sides of the body 230 from the sidewall 232. Each of the pins 240, 242 are cylindrical in shape and have a diameter of 2.5 mm and a length of 5.8 mm.

The sidewall 232 defines a curved outer profile. The curved outer profile is shaped to be received in an aperture 68, 70 of the top plate 50. The curve of the curved outer profile of the sidewall 232 accommodates the tilt of the top plate 50 relative to the bottom plate 10.

The third coupling block has a channel 248. The channel 248 is located adjacent a portion of the third coupling block having the curved outer profile. The channel 248 runs between openings on the opposed faces 234, 236. The channel 248 is for receiving a pin 90 therethrough for securing the top plate 50 to the adjuster 150.

The sidewall 232, in a portion adjacent the channel, defines a recess 250. As will be explained in more detail below, the recess 250 is sized and shaped for accommodating the central portion 164 of the bolt 156. In the exemplary embodiment shown in FIG. 5C, the recess has a curved inner profile.

The first lever arm 184 and the second lever arm 186 are substantially the same. For simplicity one lever arm 252 will be described. As a person skilled in the art will understand, the description of the single lever arm 252 applies equally to the first and second lever arms 184, 186 of each adjuster 152A, 152B, 152C.

The lever arm 252 includes a first limb 254 and a second limb 256.

The first limb 254 includes a channel 258 for receiving a pin 204 of the first coupling block 178. The first limb 254 includes a first joint member 260 for coupling to the pin 242 of the third coupling block 182. The joint member 260 includes a first protrusion 262 that extends from a shoulder 264. The first protrusion 262 includes a channel (not shown) for receiving the pin 242 of the third coupling block 182.

The second limb 256 includes a channel 266 for receiving a pin 224 of the second coupling block 180. The second limb 256 includes a second joint member 268 for coupling to a pin 242 of the third coupling block 182. The second joint member 268 includes second and third protrusions 270A, 270B spaced apart by a slot 272. The slot 272 is for receiving the first protrusion 262. The second and third protrusions 270A, 270B each include a channel 274 for receiving the pin 242 of the third coupling block 182.

In FIG. 5C, an assembled adjuster 152 is shown. The first coupling block 178 is located on the thread of the first portion 166 of the bolt 156. The second coupling block 180 is located on the thread of the second portion 168 of the bolt 156. The first and second lever arms 184, 186 are positioned on opposed sides of the first, second and third coupling blocks 178, 180, 182. The pins 202, 204 of the first coupling block 178 are positioned within respective channels 258 of respective first limbs 254 of the arms 184, 186. The pins 222, 224 of the second coupling block 180 are positioned within respective channels 266 of respective second limbs 256 of the first and second arms 184, 186. The first protrusion 262 of the first limb 254 is located within the slot 272 of the second limb 256. The pins 240, 242 of the third coupling block 182 are positioned within respective channels 258 of respective protrusions 262, 270A, 270B of respective first and second limbs 254, 256 of the first and second arms 184, 186. With the pins 240, 242 of the third coupling block 182 located within the respective channels 258 of respective protrusions 262, 270A, 270B of respective first and second limbs 254, 256 of the first and second arms 184, 186, the recess 250 of the third coupling block 182 is arranged to receive the non-threaded center portion 164 of the bolt 156.

Figure 6:
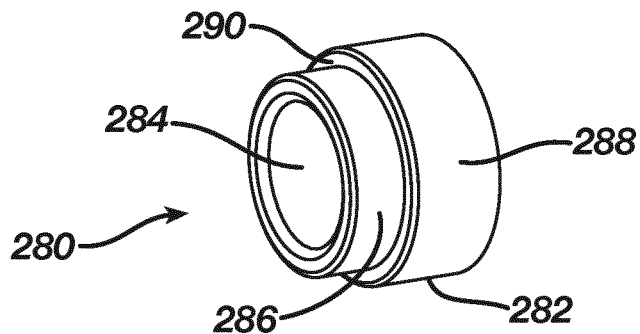
FIG. 6 shows a perspective view of a plug of the instrument of FIG. 1.

The plug 280 is shown in FIG. 6. The plug 280 is for securing an adjuster 152 to the first plate 10. The plug 280 is dimensioned and shaped to be received in the slot, or second channel, 34 of the first plate 10. The plug 280 has a body 282 that includes a channel 284 for receiving the second end 162 and non-threaded region 174 of the second portion 168 of the bolt 156. The body 282 has a first bolt region 286 and a second bolt region 288. The first and second bolt regions 286, 288 a separated by a shoulder 290. In the exemplary embodiment, the first bolt region 286 has a first diameter and the second bolt region 288 has a second diameter. The first diameter of the first bolt region is smaller than the second diameter of the second bolt region second region 288. The transition between the first and second regions 286, 288 defines the shoulder 290. The respective diameters of the first and second regions are selected such that the plugs first snuggly into the slot 34 of the first plate 10. The diameter of the first region 286 is 4.4 mm and the diameter of the second region 288 is 5.2 mm. Of course, as person of skill in the art would understand, other diameters are of course possible.

Figure 7A:
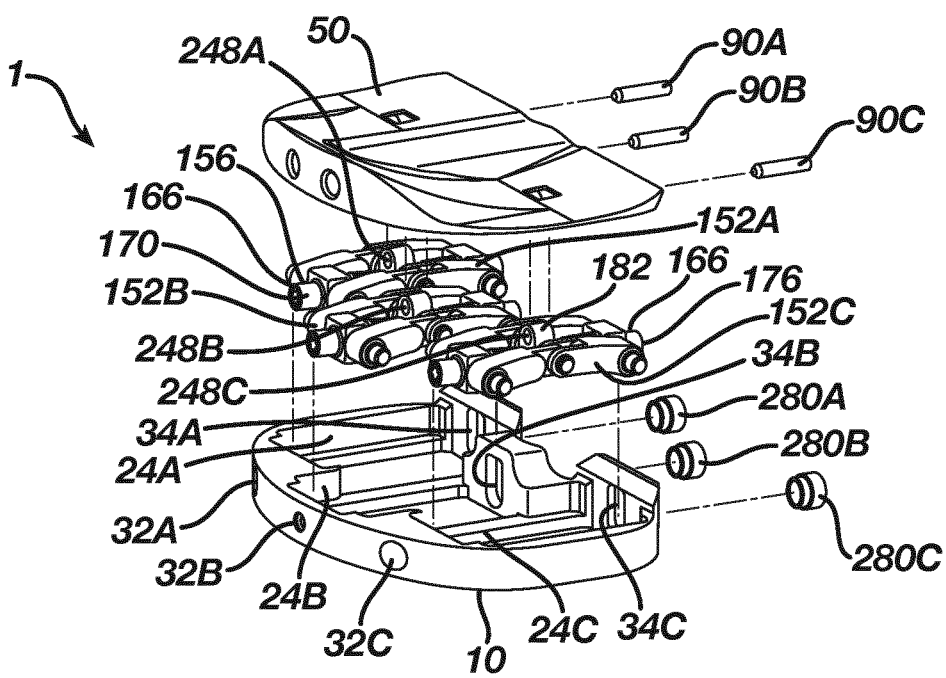
FIG. 7A shows an exploded view of the instrument of FIG. 1.

An exploded view of the instrument 1 is shown by FIG. 7A. To assemble the instrument 1, adjusters 152A, 152B, 152C are each located in stations 24A, 24B, 24C. Each non-threaded region 170 of respective first portions 166 of respective bolts 156 of the adjusters 152A, 152B, 152C are located in respective first channels 32A, 32B, 32C of the first plate 10. Each non-threaded region 176 of respective second portions 168 of respective bolts 156 of the adjusters 152A, 152B, 152C are located in respective second channels 34A, 34B, 34C of the first plate 10. With the non-threaded region 176 of respective second portions 168 of respective bolts 156 of the adjusters 152A, 152B, 152C located in respective channels 34A, 34B, 34C, respective plugs 280A, 280B, 280C are positioned through respective second channels 34A, 34B, 34C and over the non-threaded region 176 to secure the second end 162 of the bolt 156 to the first plate 10.

To secure the second plate 50 to the instrument 1, the adjusters 152A, 152B, 152C are arranged in a contracted configuration. In the contracted configured, the adjusters 152A, 152B, 152C are arranged similarly to their configuration as show in FIG. 9A. Referring again to FIG. 7A, in the contracted configuration, pins 90A, 90B and 90C are located in respective channels 248A, 248B, 248C of respective third coupling blocks 182 to hingedly couple the second plate 50 to each one of the plurality of adjusters 152A, 152B and 152C.

Figure 7B:
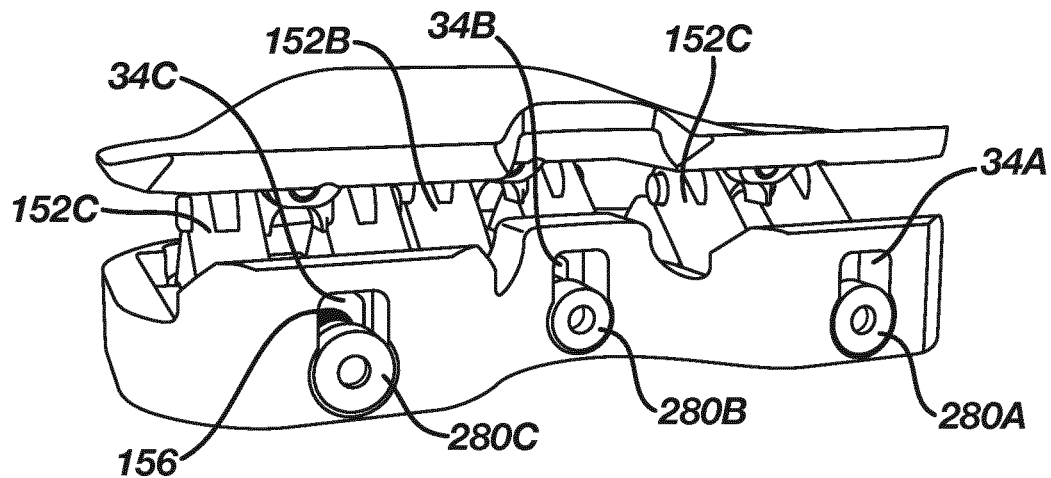
FIG. 7B shows a perspective view of the rear, or posterior, of the instrument of FIG. 1.
Figure 7C:
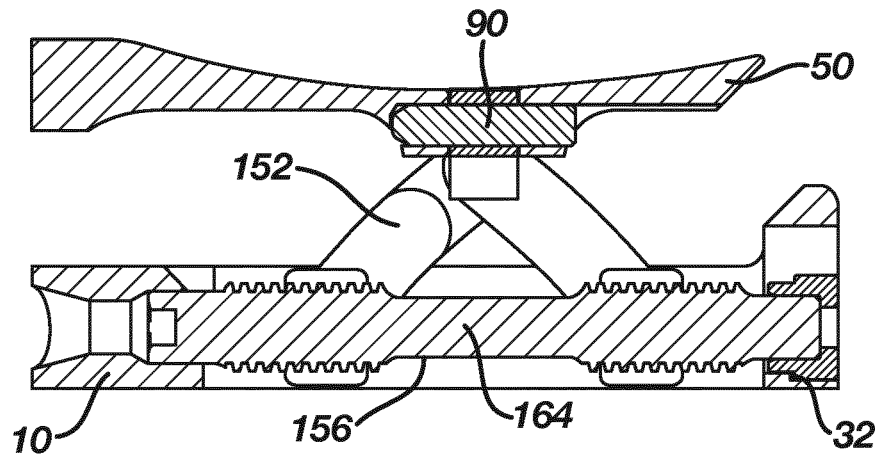
FIG. 7C shows a sectional view of the instrument of FIG. 1.

Referring to FIG. 7B, it can be seen that the plugs 280A, 280B, 280C are positioned in the channels 34A, 34B, 34C. Each plug 280A, 280B, 280C is engaged with an adjuster 152A, 152B, 152C to rotatably couple a bolt 156 of each adjuster 152A, 152B, 152C to the first plate 10. As part of the process to assemble the instrument 1, with a plug 280A, 280B, 280C appropriately positioned over a respective bolt 156 of respective adjusters 152A, 152B, 152C, said plug 280A, 280B, 280C is fixed to the respective bolt 156. The plugs 280A, 280B, 280C are fixed to their respective bolts 156 by an appropriate joining technique such as, for example, welding.

Referring to FIG. 7C, more detail can be seen showing a pin 90 arranged to rotatably, or hingedly, couple a scissor jack, or an adjuster, 152 to the top, or second, plate 50.

FIG. 7C shows how the channel 32 in combination with plug 280 rotatably couples the bolt 156 to the bottom, or first, plate 10. As a person of skill in the art would understand, the manner in which a scissor jack or adjuster 152 is coupled to the first and second plates 10, 50 is substantially the same for each adjuster 152A, 152B, 152C.

The bolt 156 has threads in the threaded regions 169, 174. The thread is of a type known to a person of skill in the art as a buttress thread. The thread is capable of taking high axial loads with reduced friction.

The second or top plate 50 is connected to the adjusters 152A, 152B, 152C with at least two degrees of freedom. The hinged connections provided by third coupling blocks 178 of each adjuster 152A, 152B, 152C to the second plate 50 provide a joint allowing the second plate to rotate with at least two degrees of freedom. The pin 90 rotatably couples the adjusters 152A, 152B, 152C to the top plate 50 with one degree of freedom. The hinged connection of the pins 240, 242 of third hinge coupling 238 rotatably couples the third coupling block 182 to the lever arms 184, 186 with a second degree of freedom.

The coupling of the adjustment assembly 150 to the first and second plates 10, 50 provides a benefit of having the first and second plates 10, 50 being retained by the adjusters 152A, 152B, 152C. The retainment facilitates insertion of the instrument 1 into the joint space of a patient's knee may have tight ligament tension. That is, due to the tight ligament tension, if the adjustment assembly 150 was not coupled to the first and second plates 10, 50, then it would be complicated to ensure the integrity of the instrument 1. For example, the second plate 50 may become dislodged or mal positioned during insertion of the instrument 1 into the joint space. As the instrument 1 is distracted, i.e. the displacement of the first and second plates 10, 50 relative to each other, the retainment of the first and second plates 10, 50 by the adjustment assembly 150 minimizes a risk of, for example, the second plate 50 becoming dislodged or mal positioned away for its connection points with each jack or adjuster 152A, 152B, 152C. Consequentially, a risk of the second plate 50 becoming distorted under distraction loading is minimized.

Various operations performed by the instrument 1 will now be described with reference to FIGS. 8A to 12D.

Figure 8B:
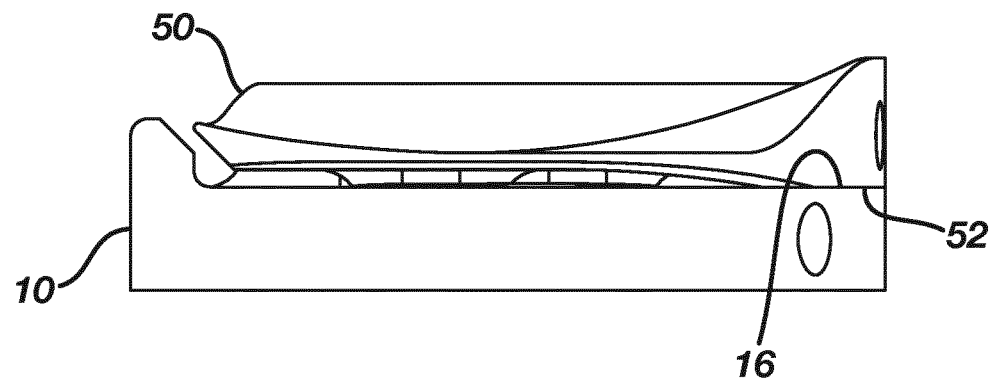

FIGS. 8A and 8B shows the instrument 1 in a closed, or insertion and removal, configuration in which the instrument 1 is configured to be inserted into and removed from a patient's knee during a surgical procedure. The total height of the instrument $TH_1$, measured from the bottom surface 12 of the first plate 10 to a maximum point 114 on the top surface 54 of the second plate 50, in the closed configuration is 8 mm.

Referring to FIG. 8B, in the closed configuration the front edge of the top surface 16 of the first plate 10 is arranged to abut the front edge of the bottom surface 52 of the second plate 50. The first and second plates 10, 50 are retained in the closed configuration due to the coupling of those plates 10, 50 to the adjusters 152A, 152B, 152C.

Figure 8C:
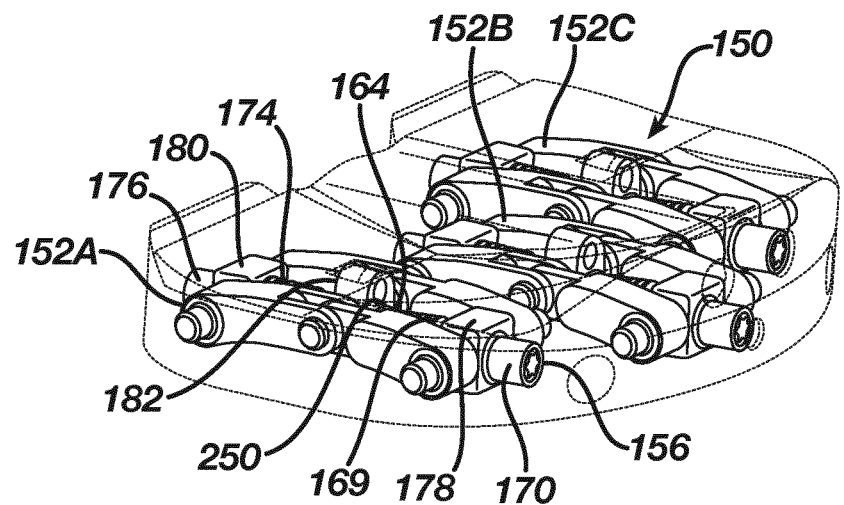
Figure 8D:
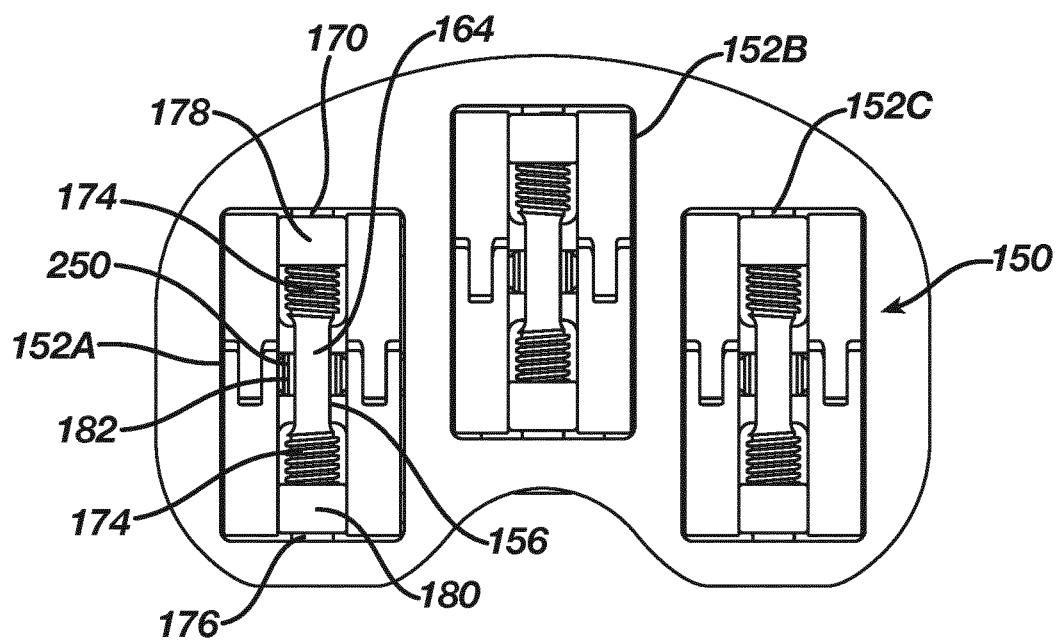

Referring to FIGS. 8C and 8D, in the closed configuration, each adjuster 152A, 152B, 152C of the adjustment assembly 150 are fully extended. In the fully extended configuration, respective first and second coupling blocks 178, 180 are positioned at the ends of the threads of the threaded regions 169, 174 of the bolt 156 that are adjacent to the non-threaded regions 170, 176. The third coupling block 182 is positioned such that the recess 250 surrounds the central portion 164 of the bolt 156.

Figure 8E:
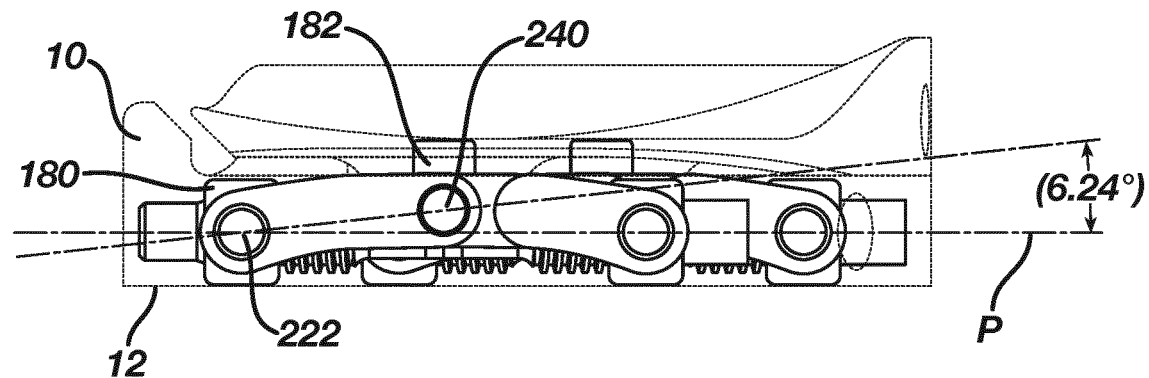

Referring to FIG. 8E, an insertion angle measured relative to a plane P running parallel to the bottom surface 12 of the first plate 10 between the center, or pivot point, of a coupling pins 222 of the second coupling block 180 and center, or pivot points, of coupling pins 240 of the third coupling block 182 is approximately 6°. In the exemplary embodiment shown, the insertion angle is 6.24°. As the skilled person would understand, the insertion angle described in relation to the relationship between the coupling pins 222 and 240 applies equally to all coupling pins 202, 204, 222, 224 of the first and second coupling blocks 178, 180 and the insertion angle formed between their respective centers and the centers of the respective pins 240, 242 of the third coupling block 182.

Figure 9A:
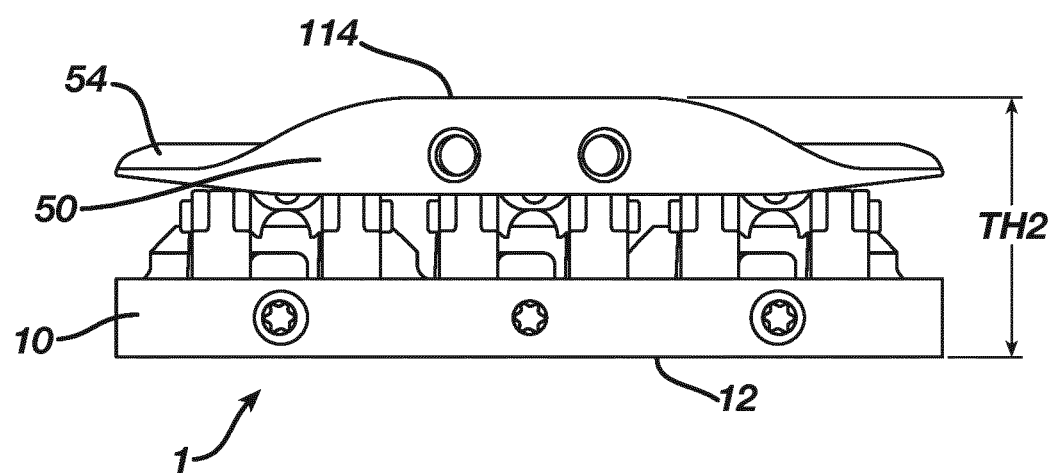
FIGS. 9A-9E show a series of views of the instrument of FIG. 1 in an extended configuration.

FIG. 9A shows the instrument 1 in a fully open configuration in which the instrument 1 is configured to place the maximum tension on a patient's knee during a surgical procedure. The height of the instrument TH2, measured from the bottom surface 12 of the first plate 10 to a maximum point 114 on the top surface 54 of the second plate 50, in the fully open configuration is 18 mm. Other heights for the instrument 1 are of course possible, as the person of skill in the art would understand.

Figure 9B:
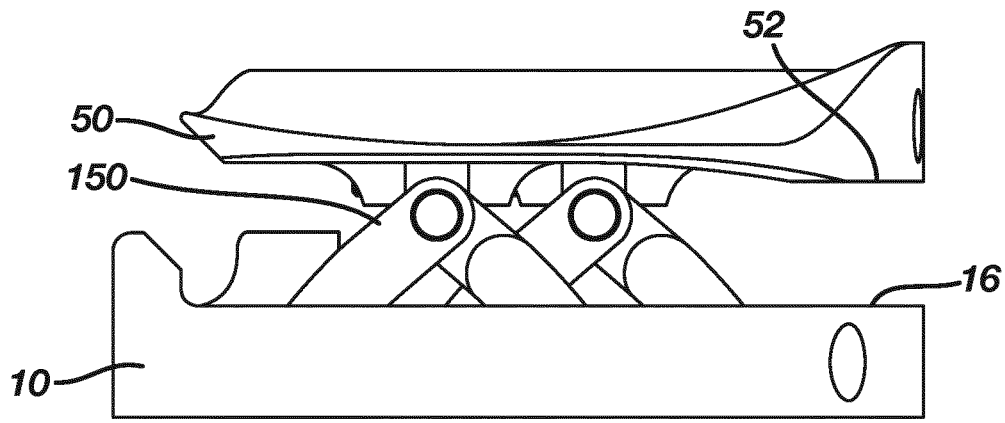

Referring to FIG. 9B, in the open configuration the first and second plates 10, 50 are spaced apart in such a way that the top surface 16 of the first plate 10 is arranged to be parallel to the bottom surface 52 of the second plate 50. In the open configuration, the second plate 50 is not tilted relative to the first plate 10. The first and second plates 10, 50 are retained in the open configuration due to the coupling of those plates 10, 50 to the adjustment assembly 150.

Figure 9C:
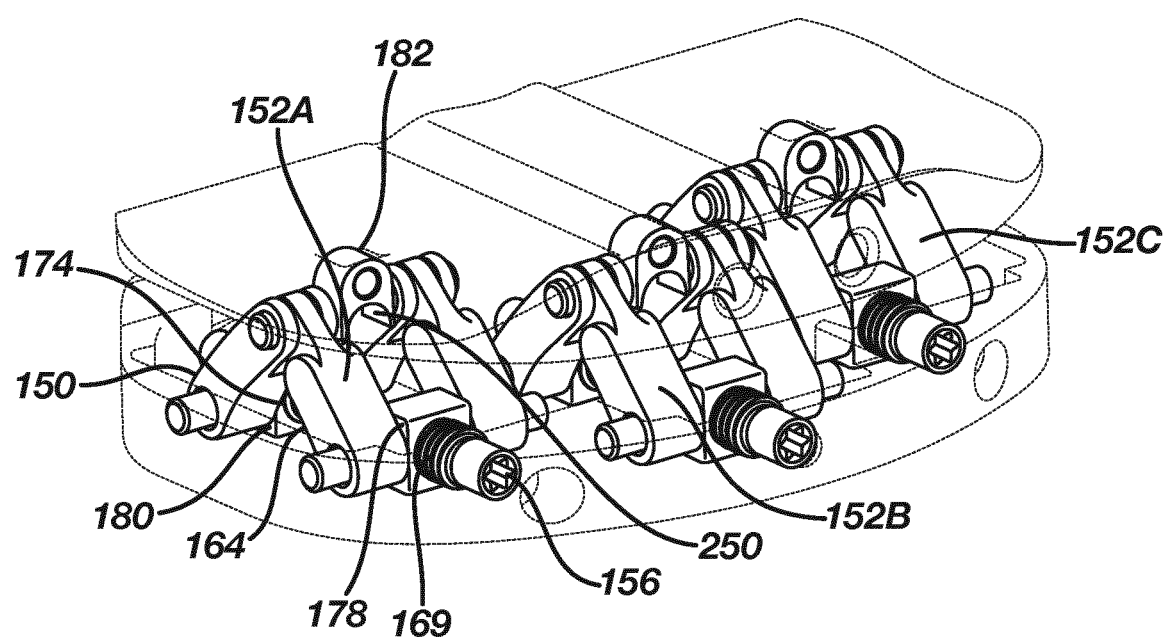
Figure 9D:
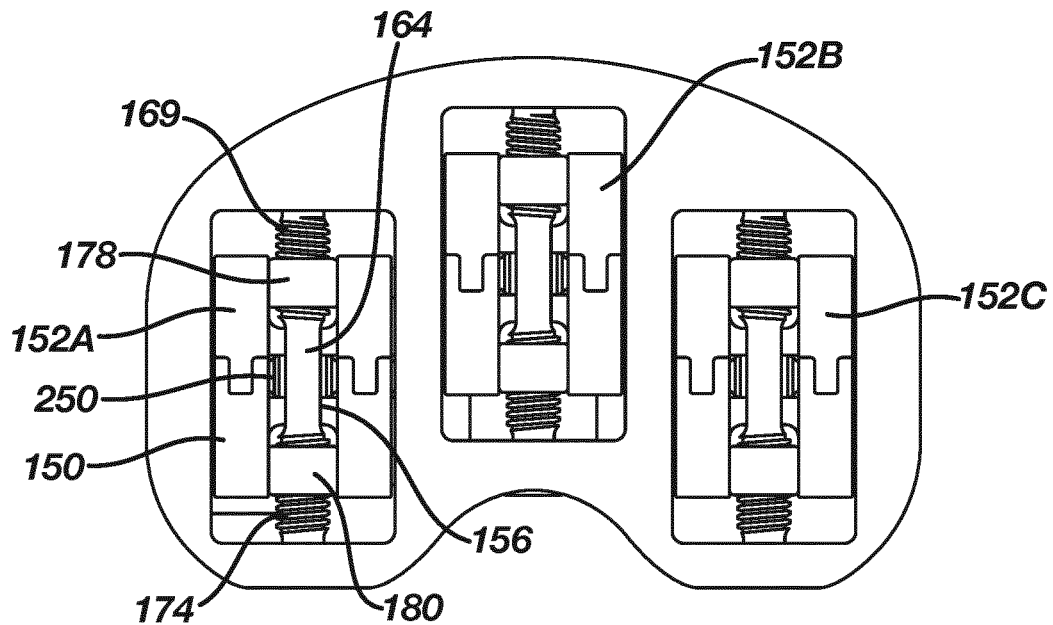

Referring to FIGS. 9C and 9D, in the open configuration, each adjuster 152A, 152B, 152C of the adjustment assembly 150 are fully contracted. Respective first and second coupling blocks 178, 180 are positioned at the ends of the threads of the threaded regions 169, 174 of the bolt 156 that are adjacent to the central portion 164. In this arrangement, the distance between the apex of the recess 250 of the third coupling block 182 and the center portion 164 of the bolt 156 is at its greatest.

Figure 9E:
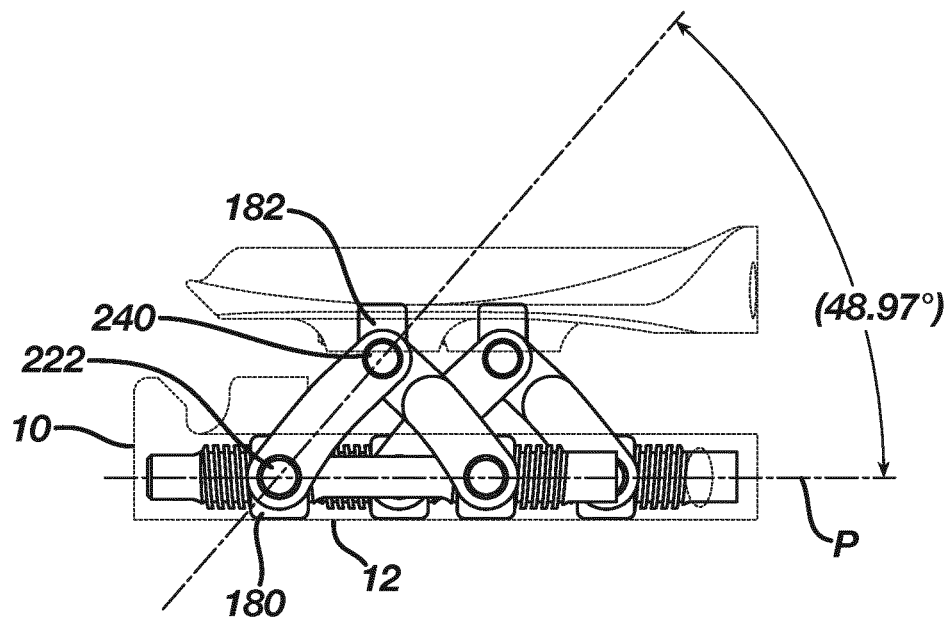

Referring to FIG. 9E, an open angle measured relative to a plane P running parallel to the bottom surface 12 of the first plate 10 between the center, or pivot point, of a coupling pins 222 of the second coupling block 180 and center, or pivot points, of coupling pins 240 of the third coupling block 182 is approximately 49°. In the exemplary embodiment shown the open angle is 48.97°. Of course the open angle is merely exemplary and as the person of skill in the art would understand the open angle could be any suitable angle. The relationship, or open angle, described between the coupling pins 222 and 240 applies equally to all coupling pins 222, 224, 240, 242 of the second and third coupling blocks 180, 182 of each adjuster 152A, 152B, 152C and the plane P.

Figure 10A:
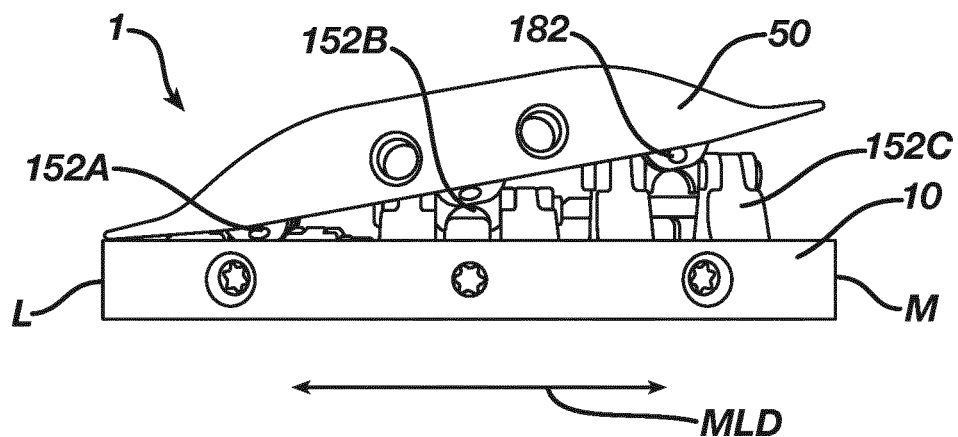
FIGS. 10A-10C show a series of views of the instrument of FIG. 1 in a medial-lateral tilted configuration.
Figure 10B:
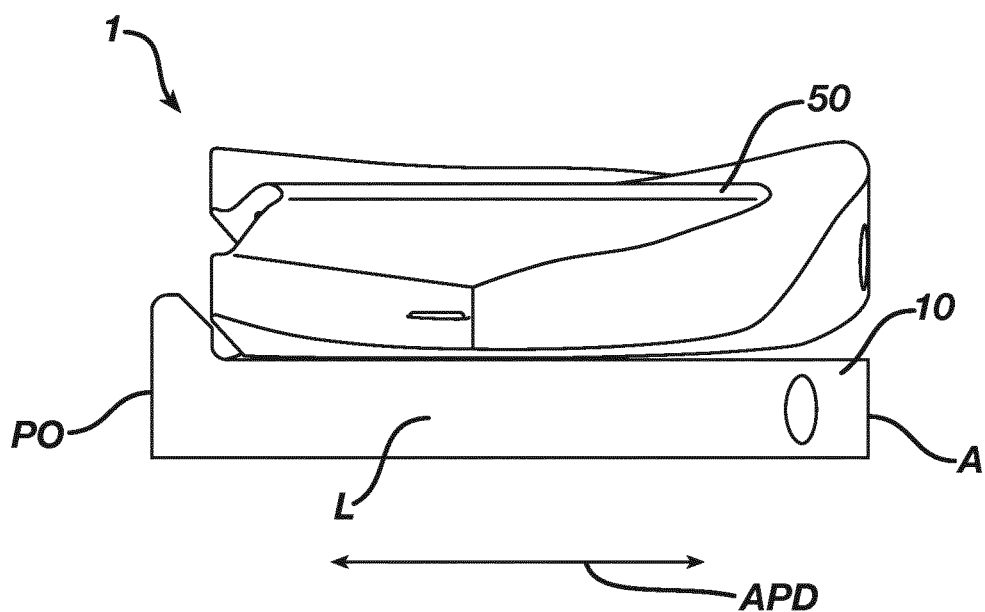

FIGS. 10A and 10B show the instrument 1 in a full medial lateral (referred to hereinafter as "ML") titled configuration in which the instrument 1 is arranged to place more tension on one side of a patient's knee during a surgical procedure than the other. For example, in the full ML tilted configuration, with the instrument 1 positioned in a patient's right knee, a medial side M of the instrument 1 would place tension on a medial side of the patient's knee (not shown). A lateral side L of the instrument 1 would apply no or minimal tension so a patient's knee.

In the full ML tilted configuration, or any ML tilted configuration between the closed configuration and the full ML tilted configuration as a person of skill in the art would understand, the second plate 50 is angled relative to the first plate 10 in a medial lateral direction MLD.

Referring to FIG. 10B, in the ML configuration, an anterior side A and a posterior side PO of the instrument 1 is not configured to apply a tension to a patient's knee (not shown) in an AP direction APD.

The description of the instrument 1 has been described in relation to a scenario where the instrument 1 is positioned in a patient's right knee. In this scenario, tension would be applied by the instrument 1 to a medial side of a patient's right knee (not shown). If the instrument 1 in the configuration shown by FIGS. 10A and 10B was positioned in a patient's left knee, then the instrument 1 would be configured to apply tension to a lateral side of the patient's left knee, i.e. the reverse of the tension that would be applied to a patient's right knee. Similarly, if the instrument 1 was configured that mirrored the configuration shown in FIG. 10A and was positioned in a patient's right knee, in that configuration the instrument 1 would be configured to apply tension to a lateral side of a patient's knee and apply minimal or no tension to a medial side of the patient's knee.

Referring again to FIG. 10A, in the exemplary full ML tilted configuration shown, an adjuster 152C located on one side of the instrument 1 is arranged to be fully extended, the adjuster 152A located on the opposed, other side of the instrument 1 is arranged to be fully contracted. To accommodate the ML tilt the adjuster 152B located in the center of the instrument 1 is adjusted as necessary.

Referring again to FIG. 10A, Due to the joint provided by the connection of respective third coupling blocks 182 to each the adjusters 152A, 152B, 152C and the second plate 50, in the ML configuration, the top plate 50 swivels relative to the bottom plate 10 and is angled relative to the bottom plate 10 to provide the ML tilt.

Figure 10C:
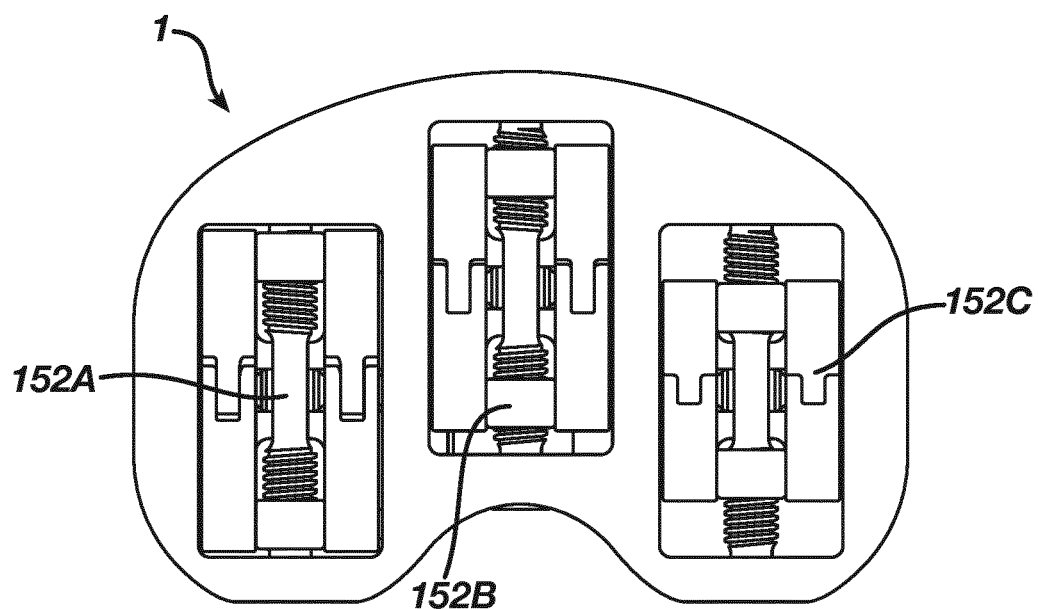

Referring to FIG. 10C, in the exemplary full ML tilted configuration, the adjusters 152A and 152C are arranged at their respective maximum and minimum heights to achieve the full ML tilt, and the central adjuster 152B is around mid-height.

In use, with the instrument 1 in the joint space of a patient's knee, in the ML tilted configuration, the instrument 1 provides a distraction force to the knee joint. Due to the coupling of the first and second plates 10, 50 to the adjustment assembly, the instrument 1 provides a reduced risk of impingement of soft tissues and surrounding ligaments in the knee joint. The reduced risk is provided since the first and second plates 10, 50 are arranged by the adjustment assembly 152 in a fixed, but adjustable, relationship relative to each other thereby minimizing a risk of those plates 10, 50 becoming unexpectedly separated from each other or moving out of position relative to each other.

Figure 11A:
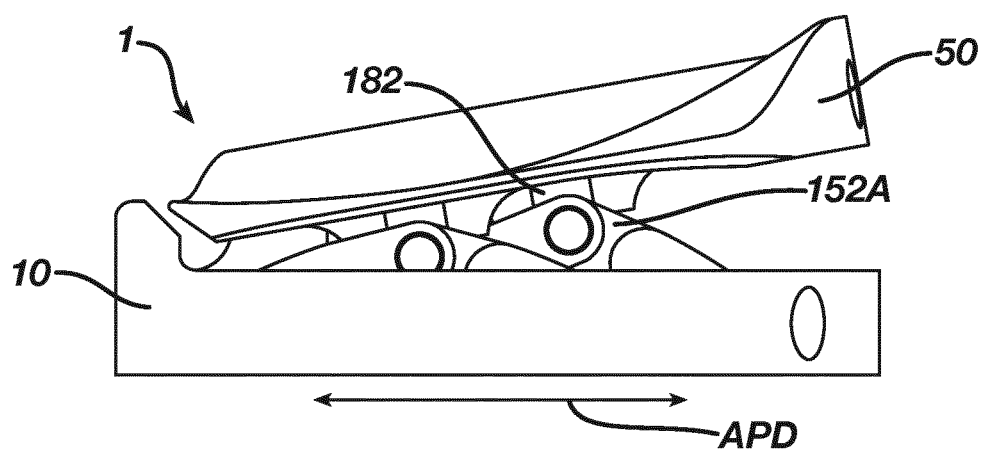
FIGS. 11A-11D show a series of views of the instrument of FIG. 1 in anterior-posterior titled configuration.
Figure 11B:
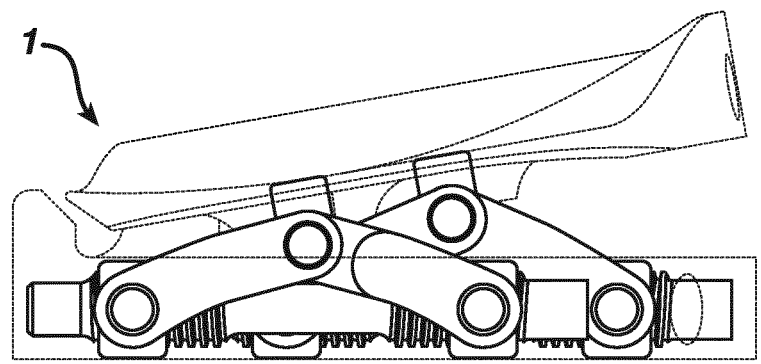

FIGS. 11A and 11B shows the instrument 1 in an anterior posterior (referred to hereinafter as "AP") titled configuration in which the instrument 1 is arranged to place more tension on the front of a patient's knee (not shown) during a surgical procedure than the back of the knee. For example, in the AP tilted configuration, with the instrument 1 positioned in a patient's knee, the instrument would place more tension on the anterior side of the patient's knee than the posterior side.

Figure 11C:
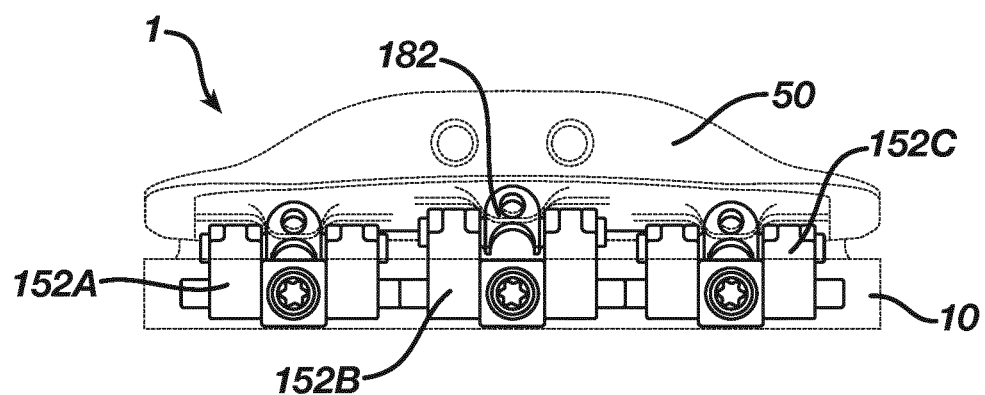
Figure 11D:
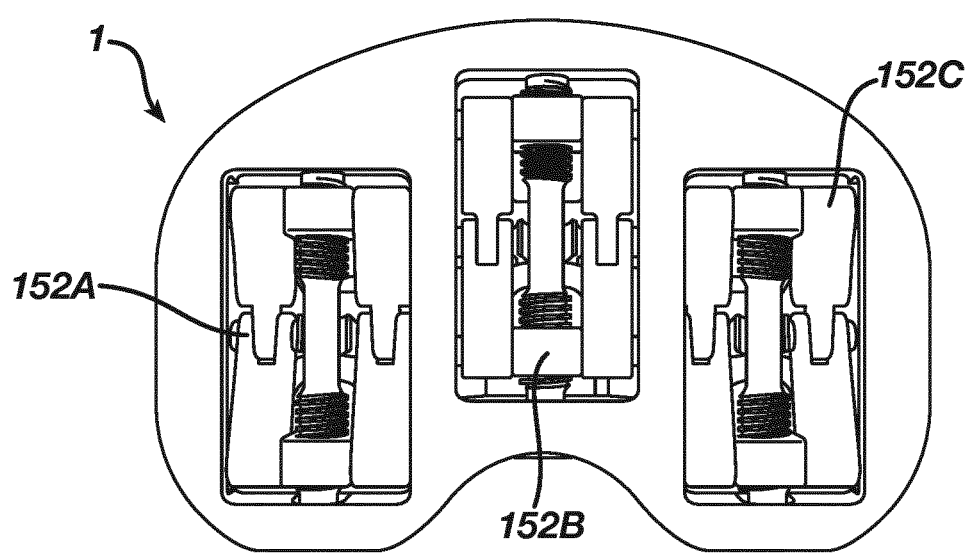

In the AP tilted configuration depicted in FIGS. 11C and 11D, the adjusters 152A and 152C located on the sides of the instrument 1 is arranged to be fully extended. The central adjuster 152B is adjusted to be part way between the fully extended and contracted arrangements. As can be seen from FIG. 11D, in the AP tilted configuration, the adjusters 152A and 152C are arranged at their minimum heights, and the central adjuster 152B is at mid-height.

Referring again to FIG. 11A, due to the joint provided by the connection of respective third coupling blocks 182 to respective adjusters 152 and the top plate 50, in the AP configuration, the top plate 50 swivels relative to the bottom plate 10 and is angled relative to the bottom plate 10 to provide the AP tilt in the anterior posterior direction APD.

In the embodiment show in FIGS. 11A-11D, the adjustment assembly 150 has three adjusters 152A, 152B, 152C that provide a three-point jack mechanism to distract the knee. A plane can be described by three points in space. The adjustment assembly 150 has three points in a triangular pattern. The triangular pattern therefore defines a plane. One point of the triangular pattern defined by the adjuster assembly 150 is provided by the adjuster 152B, which is located towards the anterior side and center of the instrument 1. The other two points are provided by the adjusters 152A, 152C which are located on the medial lateral sides posteriorly relative to the adjuster 152B. With this configuration of adjusters 152A, 152B, 12C, the instrument 1 can adjust the plane of the second plate 50 relative to the first plate 10 through actuation of the adjusters 152A, 152B, 152C. In the procedure to adjust the AP tilt, this ability to adjust the plates results in a medical practitioner being enabled to perform direct angular adjustment of the anterior posterior slope angle of the instrument 1 and consequentially of the knee joint, when the instrument 1 is in situ. The ability to facilitate direct angular adjustment of the anterior posterior slope provides direct feedback to a medical practitioner of the tibial slope angle.

FIGS. 8A-11D have been used to describe various configurations of the instrument 1. As a skilled person would understand other configurations are of course possible. For example, configurations where the adjusters 152A, 152B, 152C are used to apply varying degrees of ML tilt, varying degrees of AP tilt, and configurations in which the instrument 1 is used to apply varying degrees of both ML and AP tilt simultaneously are of course possible.

FIG. 12 shows the outrigger 300. The outrigger 300 has a first platform 302 spaced apart from a second platform 304 by a height adjuster 306. The height adjuster 306 includes a bolt 308 that is located through an aperture 310 defined in the first platform 302 and an aperture 312 in the second platform 304. The bolt 308 includes a knob 314 and a shaft 316. A longitudinal axis passes through the center of the knob 314 and runs concentrically through the shaft 316. The shaft 316 has a non-threaded region 318 and a threaded region 320. The non-threaded region 318 is located adjacent the knob 314 and the threaded region 320 runs along the longitudinal axis from the non-threaded region 318 to an end region 322. The diameter of the shaft in the non-threaded region 318 is greater than the diameter of the shaft in the threaded region 320 and the transition defines a first shoulder (not shown). The diameter of the shaft in the threaded region 320 is greater than the diameter of the shaft in a holding portion 324 of the end region 322. The holding portion 324 is adjacent the threaded region 320 and the transition between threaded region 320 and the holding portion 324 defines a second shoulder (not shown). At the end of the end region 322, which is the end of the bolt 308, a stop 326 is defined. The holding region 324 measured from the second shoulder to the stop 326 along the longitudinal axis is selected so that the second platform 304 can be positioned into a location suitable for sterilization without needing to be fully disassembled from the threaded region 320.

In the embodiment shown, the aperture 310 of the first platform 302 is non-threaded and has a recess (not shown) to receive and retain the non-threaded region 318 of the shaft 316. The threaded region 320 passes through the remainder of the first aperture 310 and is engaged with a threaded provided by the second aperture 312 of the second platform 304. With the bolt 308 coupled to the first and second platforms 302, 304 the distance between them can be altered by, for example, manipulation of the knob 314 to rotate the shaft 316 of the bolt 308.

The first platform defines a rod 328 that extends from a first surface of the first platform 302 that faces a second surface of the second platform 304. The rod 328 passes through a third aperture 330 defined by the second platform 304. The rod 328 is provided to prevent the first and second platforms 302, 304 inadvertently rotating relative to each other in use and whilst the distance between them is varied. The rod 328 also provides a means of assessing angular accuracy so that the reference plane is transferred accurately to position the final tibial resection. The rod 328 has a series of visible marks 332. The marks 332 shown in FIG. 12 are depicted as excnteding partially around, but ofc oruse they coulde extend all or some of the way around the rod 328. The marks 332 provide information to an operator suggesting an appropriate size of the bearing surface of a final implant. The marks 332 may be provided using any suitable process, for example, laser etching.

The first platform 302 has first and second protrusions 306A, 306B extending from one end of the outrigger 300. The protrusions 306A, 306b are substantially cylindrical in shape are sized and positioned to be inserted into the channels 110A, 110B of the second plate 50. The protrusions 306A, 306B have a diameter chosen so as to precisely fit into the channels 110A, 110B.

The second platform 304 has a block coupling 334 for reception in a slot of a cutting block (not shown), the cutting block used to guide the resection of a portion of the patient's bone during a surgical procedure. The block coupling 330 is a thin, relative the remainder of the second platform 304, portion and is substantially planar. The block coupling 330 has two protruding fins 336A, 336B for engaging with and partially abutting an internal wall defined by the slot of the cutting block.

The outrigger 300 includes a fourth aperture 338 on the first platform 302 and a fifth aperture 340 on the second platform 304. The fourth and fifth apertures are aligned concentrically with an axis passing through their respective centres to receive a guide rod 400, shown by the dashed lines on FIG. 13, for enabling a medical practitioner to check alignment of the tibia and femur during a surgical procedure.

The instrument 1 and the outrigger 300 are fabricated from stainless steel. For example, the instrument 1 and outrigger 300 may be fabricated from Custom 465 and 17-4SS. Of course, the instrument 1 and outrigger 300 may be fabricated from any suitable material, as the person of skill in the art would understand.

Referring to FIG. 13, the instrument 1 is used for balancing a knee. To balance the knee the plurality of adjusters 152A, 152B, 152C coupled to the first and second plates 10, 50 are actuated to vary the gap between the first and second plates 10, 50. The coupling of the second plate 50 to the adjusters 152A, 152B, 152C provides at least two degrees of freedom. Consequential to actuation of an adjuster 152 of the plurality of adjusters 152A, 152B, 152C to vary the height between the first and second plates 10, 50, the second plate 50 rotates relative to the joints coupling the adjusters 152A, 152B, 152C to the second plate 50.

Each adjuster 152 of the plurality of adjusters 152A, 152B, 152C is mechanically actuatable to vary the gap between the first and second plates 10, 50 along an adjustment axis that passes through and is transverse to the first and second plates. Each adjuster 152A, 152B, 152C has its own adjustment axis along which the height between the first and second plates 10, 50 is varied. Each joint coupling one of the adjusters 152A, 152B, 152C to the second plate 50 comprises a center of rotation aligned with a respective adjustment axis of the adjuster. The second plate 50 is configured to rotate relative to each center of rotation consequential to the gap between the first and second plates 10, 50 being varied along one of the adjustment axes. The second plate 50 rotates with two degrees of freedom relative to point at which it is coupled to the adjustment axis.

Mechanical actuation by an actuator, such as a screwdriver, varies the gap between the first and second plates 10, 50 along respective adjustment axes. The actuator is inserted into the recess 171 of one of the adjusters 152A, 152B, 152C and is rotated to vary the distance between the joint coupling one of the adjusters 152 to the second plate 50 and the first plate 10. In use, by varying the gap, the first and second plates are configured to distract a patient's knee joint.

Each adjuster is configured such that actuation of the bolt by the actuator translates the first and second coupling blocks 178, 180 equally along the longitudinal axis relative to the center portion 164 of the bolt 156. The actuation causes the distance between the first and second hinges defined by the coupling blocks 178, 180 to be varied equally relative to the center portion 164. Consequential to the distance of the first and second hinges being varied, the gap between the third coupling block 182 and the center portion 164 is varied relative to the center portion in a direction transverse to the longitudinal axis of the bolt 156. The variance of the distance between the third coupling block 182 and the center portion 164 varies the gap between the first and second plates 10, 50.

The joints coupling the second plate 50 to respective adjusters 152A, 152B, 152C constrains the second plate. Consequentially, as the gap is varied by one of the adjusters 152A along its respective adjustment axis, the gap along the respective adjustment axis between the first plate 10 and the joint coupling the other adjusters 152B, 152C to the second plate 50 remains the same. Thus, as the gap is varied, the second plate 50 rotates relative each joint or center of rotation consequential to the gap being varied along one of the adjustment axes.

The plurality of adjusters consists of three adjusters mechanically actuatable to vary the gap along their respective adjustment axes. A person of skill in the art would understand that more adjusters are of course possible. When viewed in plan, the points at which the respective adjustment axes traverse the first and second plates are coaxial and form a triangular arrangement.

The outrigger 300 is coupled to the instrument 1 when an appropriate knee balance has been identified. The protrusion of the first plate 302 of the outrigger are inserted into the channels 110A, 110B of the second plate. After checks are completed, an operator assembles a cutting block to the outrigger 300 by positioning it on the block coupling 330 and resects a bone. The outrigger 300 is also known as a resection guide. As will be described in more detail below, coupling the outrigger 300 to the instrument 1, facilitates resection of a femur or tibia in a plane parallel to the articulating surface provided by the second plate 50 in which the femur is located, in use. Such a planar resection enables ligament tension be to accounted for when resurfacing either the tibia or femur.

FIG. 13 shows an instrument 1 and outrigger 300 in situ in a patient's knee during a surgical procedure. During the surgical procedure, the instrument assembly provides a means of assessing kinematic balance of the medial and lateral ligaments and other soft tissues surrounding the knee, prior to committing to primary resections on the proximal tibial and distal femur.

The surgical procedure may be a femur first total knee arthroplasty. The procedure may involve performance by a physician of a conservative proximal tibial resection. After the conservative resection, the physician assess the resection to ensure that the proximal tibia has been fully resurfaced leaving the maximum possible bone. The physician then completes all femoral resections using manual instruments by referencing anatomical bony landmarks and mechanical alignment principles known to a person of skill in the art. A femoral trial FT is then placed onto resected femur F.

After positioning the femoral trial FT into the space between the distal end of the femur F and the proximal end of the tibia T, the joint space is prepared for receipt of the instrument 1. The instrument 1 is inserted into the joint space. The instrument 1 is positioned so that the femur can articulate freely on the top surface of the second plate 50. The ability to articulate the femur on the top surface of the second plate reduces the need to insert a separate bearing surface, which may add additional thickness and reduce the ability to achieve the minimum collapsed height of the instrument 1.

The physician then places the patient's knee in full flexion and full extension. An actuator (not shown), such as a screw driver, is then used to adjust each of the adjusters 152A, 152B, 152C to apply a distraction force to the knee joint. The physician continues to make adjustments to the adjusters 152A, 152B, 152C until they believe the patient's knee is equal balanced. The posterior capsule of the knee joint is then released, and the physician will use the instrument 1 to ensure that the patient's knee joint has approximately 30 degrees of flexion.

The physician uses the instrument 1 to distract the joint such that the knee joint is in equal balance both medially and laterally as a well as anteriorly and posterior. The physician may configure the instrument from the initial configuration depicted by FIGS. 8A-8E to any configuration, such as the full ML tilt shown by FIGS. 10A-10C or the full AP tilt shown by FIGS. 11A-11D, up to the maximum height configuration depicted by FIGS. 9A-9E. The physician adjusts the instrument 1 to achieve an equally balanced knee.

With the joint in equal balance, the outrigger 300 is coupled to the instrument 1. The height of outrigger 300 is adjusted to a desired resection configuration. In this configuration, the proximal surface of the tibia is to be fully resurfaced and prepared for a tibial implant. In this way, the coupling of the outrigger 300 to the second plate 50 and subsequent adjustment provides a mechanism to directly transfer the plane, determined to provide an appropriate balance, of the second plate 50 to the proximal tibia.

Before performing the resection, a physician may check the tibia with an angle wing (not shown) or similar planer referencing device as a person of skill in the art would understand.

A tibial cutting block (not shown) may then be located on the block coupling 330. Of course, the cutting block may have already been located on the block coupling 330 before the outrigger 300 was coupled to the instrument 1 as a person of ordinary skill in the art would understand. After optionally making final assessments of the knee joint, the physician pins the tibial cutting block to the tibia T. The instrument 1 and outrigger 300 are removed for the patient's knee joint and the final tibial resection performed.

Optionally, before a resection is performed a long leg alignment rod R is inserted into the outrigger 300 to check mechanical alignment of the femur and tibia. The rod R may be used when the instrument 1 and outrigger 300 are being used with an implant system designed for parallel gaps between the femur and tibia, and mechanical alignment within validated limits.

Alternatively, the instrument 1 can be used for a tibial first surgical procedure. In this procedure, the final tibial resection is first performed using known tibial landmarks as a person of skill in the art would understand. The instrument 1 is inserted into the patient's knee joint and the balance of the knee is assessed as described previously. That is the full range of flexion and extension of the knee joint is assessed.

Once the physician believes an optimal balanced knee has been identified, a balance plane has been established. The balance plane is the plane defined by the second plate 50 and its relationship with the plane defined by the first plate 10. The outrigger 300 is then coupled to the instrument 1. In the tibial first procedure, the outrigger 300 is coupled to the instrument in an inverted configuration that is the opposite of the configuration shown on FIG. 13.

The outrigger 300 is adjusted to the height of the final femur resection, and distal femur resection block that is connected to the block coupling 330 is pinned to the femur. In this way, the instrument 1 and outrigger 300 enable simple and direct transfer of the tibia plane and the balance plane to the femoral resection plane.

With the distal femur resection block so pinned, the final distal resection of the femur is performed. The physician then completes sizing rotation, anterior/posterior and chamfer resections using traditional instruments (not shown) as a person of ordinary skill in the art would understand.

The instrument 1 enables simple resurfacing the tibia or femur. For example, the procedures do not require milling counterbored holes into the bone to be used as a reference point to locate a secondary milling guide plate. Once a physician believes they have the most appropriately balanced knee, the simply pin a cutting block and perform the final bone resection.

The instrument 1 enables a surgical procedure with minimal milling or burring of a patient's bones, that has reduced inaccuracies associated with milling counterbored holes and having to transfer balanced plane information between instruments.

The instrument 1 enables a surgical procedure that involves a simple transfer of a planer reference from the second plate 50 to a cutting block (not shown) through use of the outrigger 300.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

Although preferred embodiment(s) of the present invention have been shown and described, it will be appreciated by those skilled in the art that changes may be made without departing from the scope of the invention as defined in the claims.

In this specification, the terms "comprise", "comprises", "comprising" or similar terms are intended to mean a non-exclusive inclusion, such that a system, method or apparatus that comprises a list of elements does not include those elements solely, but may well include other elements not listed.

The reference to any prior art in this specification is not, and should not be taken as, an acknowledgement or any form of suggestion that the prior art forms part of the common general knowledge.

We claim:

1. An instrument for balancing a knee comprising:
a first plate, and
a second plate, and
a plurality of adjusters coupled to the first and second plates and actuatable to vary a gap between the first and second plates;
wherein each adjuster of the plurality of adjusters is coupled to the second plate by a joint having at least two degrees of freedom;
wherein each adjuster of the plurality of adjusters comprises a half-scissor jack, each half scissor jack comprising a pivot that is part of the joint;
wherein the jack of each adjuster of the plurality of adjusters comprises:
a bolt extending from a first end to a second end along a longitudinal axis, the bolt shaped and dimensioned to be received and rotatably held in a channel in the first plate, the bolt having a center portion dividing the bolt into a first portion from the first end to the center portion and a second portion from the second end to center portion, the first portion comprising an external left hand thread and the second portion comprising an external right hand thread, one of the first or second ends configured to he engaged by an actuator for rotating the bolt;
a first coupling block arranged on the first portion of the bolt, the first coupling block comprising a channel having an internal thread configured to mate with the left hand thread of the first portion;
a second coupling block arranged on the second portion of the bolt, the second coupling block comprising a channel having an internal thread configured to mate with the right hand thread of the second portion;

a first lever arrangement extending from a first end to a second end, and a second lever arrangement extending from a first end to a second end;

a first hinge coupling the first end of the first lever arrangement to the first coupling block;

a second hinge coupling the first end of the second lever arrangement to the second coupling block;

a third hinge coupling together the second ends of the first and second lever arrangement adjacent the center portion, the third hinge forming the pivot of the jack;

wherein each adjuster is configured such that actuation of the bolt by the actuator translates the first and second coupling blocks equally along the longitudinal axis relative to the center portion to thereby cause a distance between the first and second hinges to be varied equally relative to the center portion and consequential to the distance between the first and second hinges being varied a gap between the pivot and the center portion is varied in a direction transverse to the longitudinal axis in order to vary the gap between the first and second plates.

2. The instrument of claim 1, wherein, consequential to actuation of an adjuster of the plurality of adjusters and the joint coupling the adjuster to the second plate, the second plate rotates relative to the joint.

3. The instrument of claim 1, wherein each adjuster of the plurality of adjusters is mechanically actuatable to vary the gap between the first and second plates along a respective adjustment axis that is transverse to the first and second plates; and the joint coupling each one of the adjusters to the second plate comprises a center of rotation aligned with the respective adjustment axis; and wherein the second plate is configured to rotate relative to each center of rotation consequential to the gap being varied along one of the adjustment axes.

4. The instrument of claim 1, wherein the joint coupling each one of the adjusters to the second plate comprises a center of rotation about which the second plate rotates with two degrees of freedom, each center of rotation is aligned with a respective adjustment axis that traverses the first and second plates; and wherein mechanical actuation of one of the adjusters varies the gap along its respective adjustment axis between the first plate and the joint coupling said adjuster to the second plate.

5. The instrument of claim 1, wherein the joint comprises a first pin joint and a second pin joint, the first pin joint provides a first degree of the two degrees of freedom and the second pin joint provides a second degree of the two degrees of freedom;

wherein the second plate is configured to rotate relative to the first and second pin joints of the joint whilst an adjuster of the plurality of adjusters is mechanically actuated to vary the gap between the first and second plates.

6. The instrument of claim 1, wherein a top surface of the first plate is arranged to face a bottom surface of the second plate; and wherein the plurality of adjusters are arranged between the top and bottom surfaces.

7. The instrument of claim 6, wherein the plurality of adjusters consists of three adjusters arranged in a triangular configuration.

8. The instrument of claim 1, wherein each adjuster of the plurality of adjusters comprises a half-scissor, jack, each half scissor jack comprising a pivot that is part of the joint.

9. The instrument of claim 8, wherein each jack comprises:

a bolt extending from a first end to a second end along a longitudinal axis, the bolt having a center portion dividing the bolt into a first portion from the first end to the center portion and a second portion from the second end to center portion, the first portion comprising an external left hand thread and the second portion comprising an external right hand thread, one of the first or second ends configured to he engaged by an actuator for rotating the bolt;

a first coupling block arranged on the first portion of the bolt, the first coupling block comprising a channel having an internal thread configured to mate with the left hand thread of the first portion;

a second coupling block arranged on the second portion of the bolt, the second coupling block comprising a channel having an internal thread configured to mate with the right hand thread of the second portion;

a first lever arrangement extending from a first end to a second end, and a second lever arrangement extending from a first end to a second end;

a first hinge coupling the first end of the first lever arrangement to the first coupling block;

a second hinge coupling the first end of the second lever arrangement to the second coupling block;

a third hinge coupling together the second ends of the first and second lever arrangement adjacent the center portion, the third hinge forming the pivot of the jack;

wherein each adjuster is configured such that actuation of the bolt by an actuator translates the first and second coupling blocks equally along the longitudinal axis relative to the center portion to thereby cause the distance between the first and second hinges to be varied equally relative to the center portion and consequential to the distance of the first and second hinges being varied the gap between the pivot and the center portion is varied relative to the center portion in a direction transverse to the longitudinal axis in order to vary the gap between the first and second plates.

10. The instrument of claim 1, wherein each of the first and second plates comprises top and bottom surfaces connected by a wall, the top surface of the first plate and the bottom surface of the second plate are arranged to face each other;

wherein each adjuster of the plurality of adjusters is coupled at a discrete location to the top surface of the first plate and the bottom surface of the second plate and space the top and bottom surfaces apart along a respective adjustment axis that traverses the first and second plates;

wherein the joint of each of the plurality of adjusters couples one of the adjusters to the bottom surface of the second plate in alignment with its respective adjustment axis, the joint enabling the second plate to rotate about first and second axes that extend orthogonally with respect to each other and with respect to its respective adjustment axis;

wherein, when one of the adjusters is actuated, the gap between the bottom surface of the second plate is varied relative to the top surface of the first plate and consequentially the bottom surface rotates about the first and second axes of the joint.

11. The instrument of claim 1, wherein:

the first plate lies substantially in a first plane;

the second plate lies substantially in a second plane; and
the plurality of adjusters comprises three adjusters; and
wherein the three adjusters are arranged in between the first and second plates in a triangular arrangement relative to the first and second planes.

12. The instrument of claim 1, wherein the second plate comprises at least one recess to accommodate the joint coupling at least one of the adjusters of the plurality of adjusters to the second plate.

13. The instrument of claim 1, wherein the second plate comprises connector to receive and hold an outrigger.

14. A kit comprising:
an instrument of claim 13 for balancing a knee; and
an outrigger;
wherein the outrigger comprises a body, the body comprising: a connection component configured to he received and held by the connector; and
a slot arranged to align a blade of a surgical saw with a portion of the knee to be cut.

15. The instrument of claim 12, wherein the at least one recess is a cut through in the second plate.

16. The instrument of claim 1, wherein the first plate is configured to be placed on a tibial side of a knee and the second plate is arranged relative to the first plate to be engaged with a femoral side of the knee by actuation of at least one of the plurality of adjusters.

\* \* \* \* \*